United States Patent
Yui

(10) Patent No.: US 9,599,454 B2
(45) Date of Patent: Mar. 21, 2017

(54) OPTICAL INTERFEROMETER, DATA ACQUISITION DEVICE, AND DATA ACQUISITION METHOD

(71) Applicant: TOKYO UNIVERSITY OF SCIENCE FOUNDATION, Tokyo (JP)

(72) Inventor: Hiroharu Yui, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 260 days.

(21) Appl. No.: 14/348,495

(22) PCT Filed: Sep. 27, 2012

(86) PCT No.: PCT/JP2012/074962
§ 371 (c)(1),
(2) Date: Mar. 28, 2014

(87) PCT Pub. No.: WO2013/047698
PCT Pub. Date: Apr. 4, 2013

(65) Prior Publication Data
US 2014/0253919 A1   Sep. 11, 2014

(30) Foreign Application Priority Data

Sep. 30, 2011 (JP) .................. 2011-218220

(51) Int. Cl.
*G01J 3/45* (2006.01)
*G01J 3/44* (2006.01)
(Continued)

(52) U.S. Cl.
CPC ............ *G01B 9/02041* (2013.01); *G01J 3/44* (2013.01); *G01J 3/4535* (2013.01); *G01J 9/04* (2013.01);
(Continued)

(58) Field of Classification Search
CPC .. G01J 3/44; G01J 3/4535; G01J 9/04; G01N 21/65; G01N 2021/655; G01N 2021/653; G01B 9/02041
(Continued)

(56) References Cited

U.S. PATENT DOCUMENTS

2006/0192969 A1* 8/2006 Marks .................. G01J 3/4412
356/451
2008/0037595 A1   2/2008 Gankkhanov et al.
(Continued)

FOREIGN PATENT DOCUMENTS

JP    05005698 B2    1/1993
JP    2008529062 A   7/2008
(Continued)

OTHER PUBLICATIONS

Marks et al., "Interferometric Differentiation Between Resonant Coherent Anti-Stokes Raman Scattering and Nonresonant Four-Wave-Mixing Processes", Applied Physics Letters, vol. 85, No. 23, Dec. 6, 2004, 3 pages.
(Continued)

*Primary Examiner* — Sunghee Y Gray
(74) *Attorney, Agent, or Firm* — Marshall, Gerstein & Borun LLP

(57) ABSTRACT

An optical interferometer includes: a light source that emits a coherent first beam and a second beam that has a frequency difference corresponding to the natural frequency of a target molecule; amplitude modulating means that modulates the amplitude of the second beam; splitting means that splits the first beam into a reference beam and a first applied beam; optical path length adjusting means that adjusts the optical path length of the reference beam; and detecting means that detects an interference pattern between the reference beam and the first beam (a signal beam) that has experienced a
(Continued)

stimulated Raman loss or gain in accordance with the amplitude modulation as a result of the frequency difference resonating with the target molecule when the first applied beam and a second applied beam (the amplitude modulated second beam) have been applied to a measurement position of an object.

10 Claims, 23 Drawing Sheets

(51) Int. Cl.
    *G01B 9/02*     (2006.01)
    *G01J 3/453*     (2006.01)
    *G01N 21/65*     (2006.01)
    *G01J 9/04*     (2006.01)

(52) U.S. Cl.
    CPC ....... *G01N 21/65* (2013.01); *G01N 2021/655* (2013.01)

(58) Field of Classification Search
    USPC ................ 356/451, 301, 479, 484, 450, 497
    See application file for complete search history.

(56) References Cited

U.S. PATENT DOCUMENTS

| | | | |
|---|---|---|---|
| 2010/0046039 A1 | 2/2010 | Xie et al. | |
| 2010/0177307 A1 | 7/2010 | Rimke et al. | |
| 2012/0307238 A1* | 12/2012 | Fujita | G02B 21/002 356/301 |

FOREIGN PATENT DOCUMENTS

| | | | | |
|---|---|---|---|---|
| JP | 2010048805 A | | 3/2010 | |
| JP | 2010145270 A | | 7/2010 | |
| JP | 2010526345 A | | 7/2010 | |
| JP | 2011158413 A | | 8/2011 | |
| JP | WO2011099269 | * | 8/2011 | ........... G02B 21/002 |

OTHER PUBLICATIONS

Marks et al., "Nonlinear Interferometric Vibrational Imaging", Physical Review Letters, vol. 92, No. 12, Mar. 26, 2004, 4 pages.
Jurna et al., "Shot Noise Limited Heterodyne Detection of Cars Signals", Proceedings of SPIE, SPIE—International Society for Optical Engineering, vol. 6860, Jan. 1, 2008, 10 pages.
Extended European Search Report in EP Application No. 12837200.0 dated Jul. 3, 2015, 12 pages.
International Search Report for PCT/JP2012/074962 dated Dec. 25, 2012.

* cited by examiner

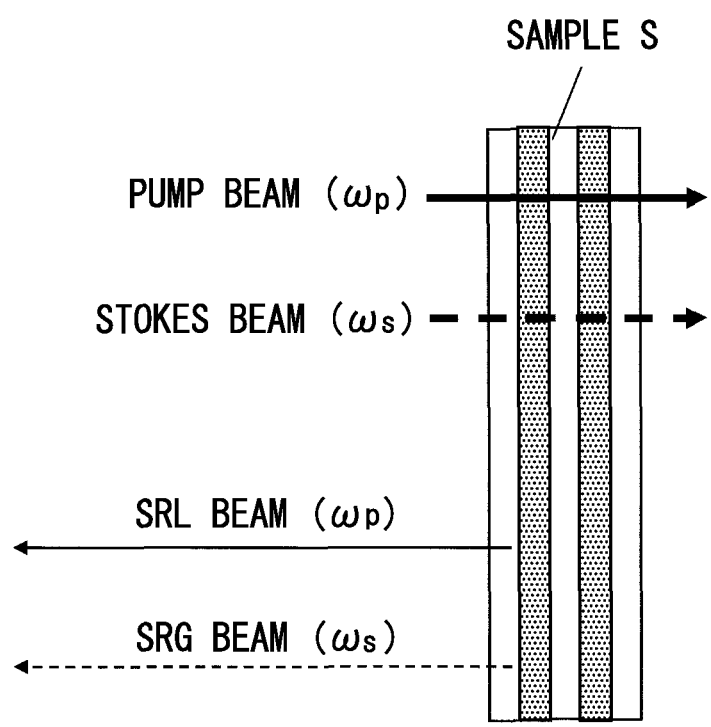

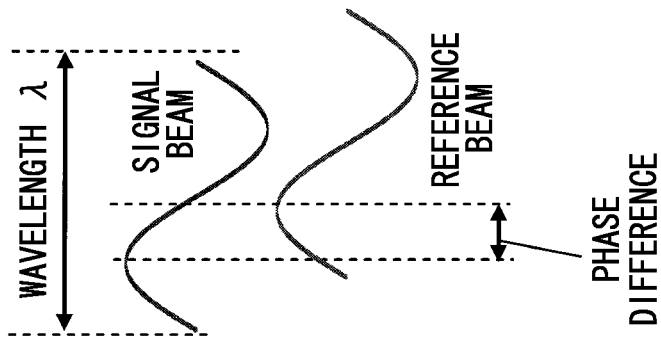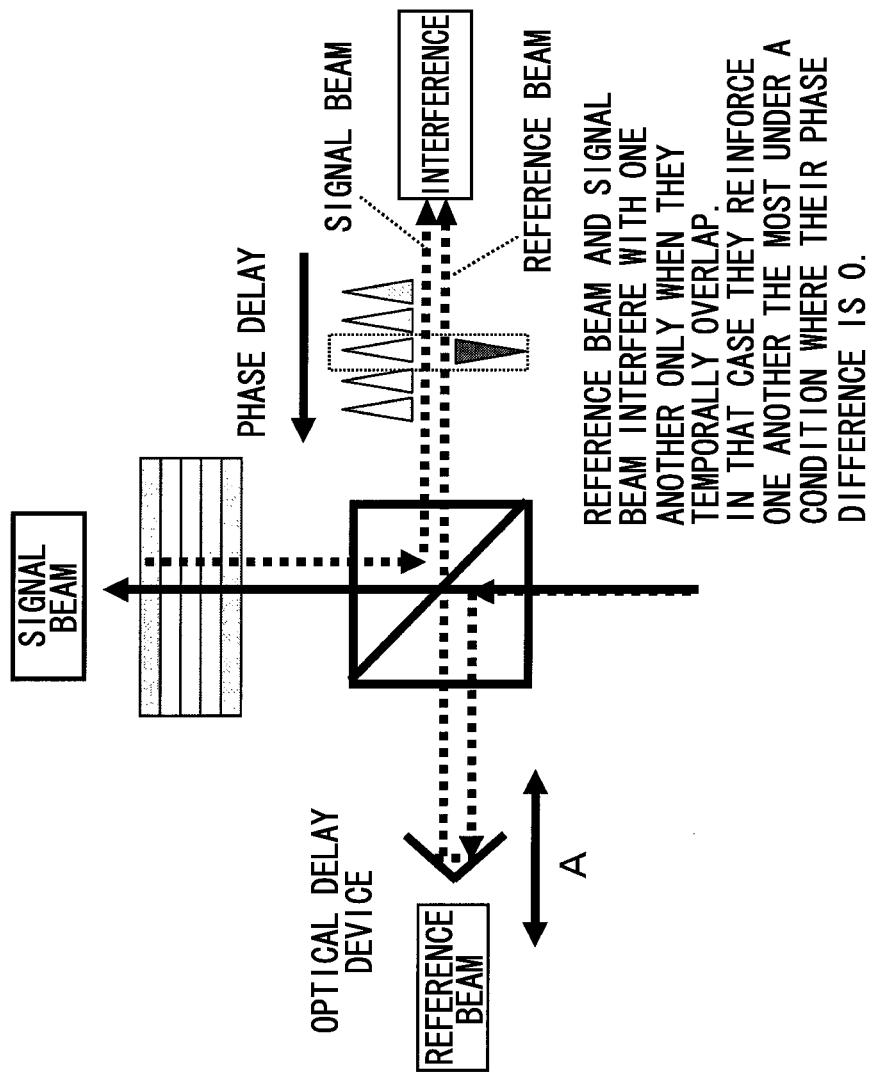

INTERFEROGRAM WHEN THERE IS RESONANCE IN TARGET MOLECULE

TIME (ps)

SPECTRUM WHEN THERE IS TARGET MOLECULE RESONANCE

SRS BEAM INTERFERENCE SIGNAL APPEARS AS SIDE BANDS AT $\pm f'$ MHz $f-f'$  $f$  $f+f'$   FREQUENCY(MHz)

INTERFEROGRAM WHEN THERE IS NO RESONANCE

TIME (ps)

SPECTRUM WHEN THERE IS NO RESONANCE

BEAT FREQUENCY $f$ MHz $f$  FREQUENCY (MHz)

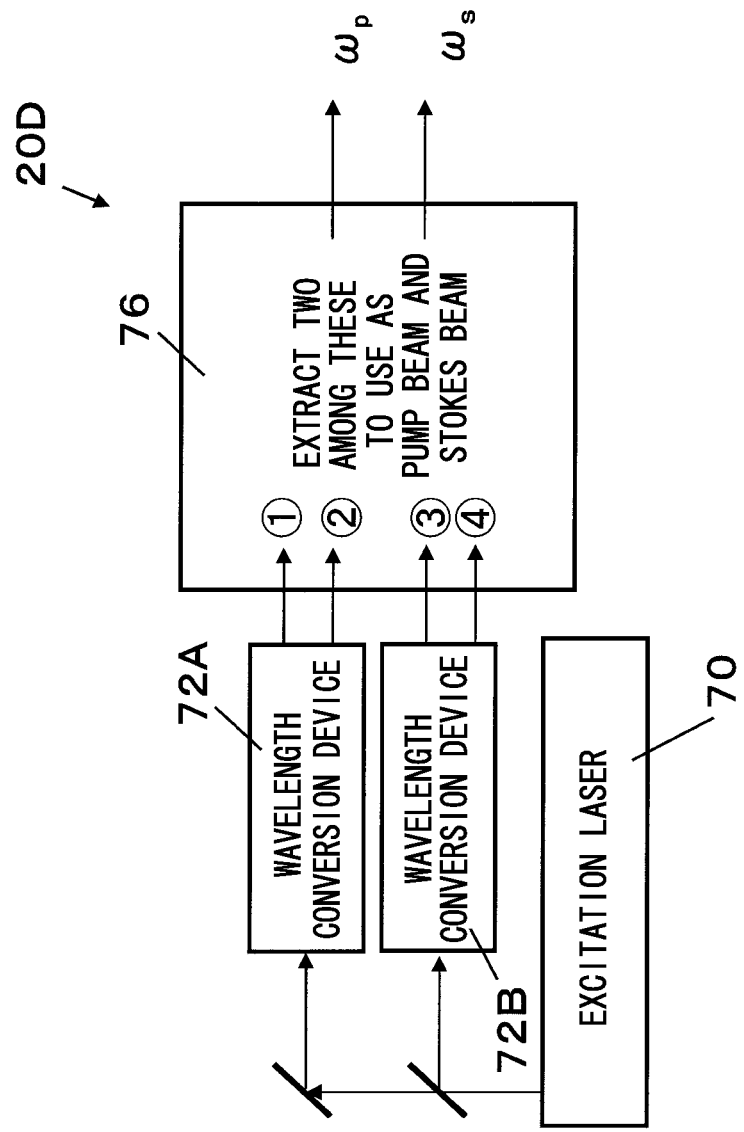

OPTICAL INTERFEROMETER, DATA ACQUISITION DEVICE, AND DATA ACQUISITION METHOD

TECHNICAL FIELD

The present invention relates to an optical interferometer, a data acquisition device, and a data acquisition method.

BACKGROUND ART

Conventionally, Raman microscopes, which obtain an image by detecting Raman scattered light that is produced when a laser beam has been applied to a sample, have been known. With a Raman microscope, molecules included in a sample can be identified and the two-dimensional distribution of those molecules can be observed from the Raman scattering spectrum of the sample.

In Japanese Patent Application Laid-open (JP-A) No. 2011-158413, for example, there is disclosed a laser microscope device including: two optical paths that guide pulse laser beams having two different frequencies that have a frequency difference equal to the frequency of a specific molecular vibration of a molecule in a sample; multiplexing means that multiplexes the pulse laser beams guided thereto on the two optical paths; frequency modulating means that is disposed on at least one of the two optical paths and modulates the frequency dispersion amounts of the pulse laser beams guided on the two optical paths; pulse laser beam amplitude modulating means that is disposed on at least one of the two optical paths and modulates the amplitudes of the pulse laser beams guided on the two optical paths; and modulation signal detecting means that condenses, in the sample, the two pulse laser beams multiplexed by the multiplexing means and detects, in synchronization with the modulation by the pulse laser modulation unit, stimulated Raman scattering produced from the specific molecular vibration of the molecule in the sample.

However, the microscope image obtained by a Raman microscope is a two-dimensional image, and the distribution of molecules in the depth direction of the sample cannot be closely observed, even if the focal depth direction is changed, because the signals from all of the optical paths of the laser beams are superposed.

SUMMARY OF INVENTION

Technical Problem

It is an object of the present invention to provide an optical interferometer, a data acquisition device, and a data acquisition method that can utilize the stimulated Raman scattering process to obtain scattered beam phase data and molecule identification data identifying molecular species. Furthermore, it is another object of the present invention to provide a data acquisition device and a data acquisition method which, on the basis of the scattered beam phase data and the molecule identification data obtained utilizing the stimulated Raman scattering process, can acquire image data representing a three-dimensional image or a tomographic image of a subject in which a molecule identification function has been added to a phase interference image.

Solution to Problem

A first aspect of the present invention is an optical interferometer including: a light source that emits a coherent first beam and a second beam that has, with respect to the frequency of the first beam, a frequency difference corresponding to the natural frequency of a target molecule; amplitude modulating means that modulates the amplitude of the second beam; splitting means that splits the first beam into a reference beam and a first applied beam; optical path length adjusting means that adjusts the optical path length of the reference beam; and detecting means which, taking as a second applied beam the second beam whose amplitude has been modulated and taking as a signal beam the first beam that has experienced a stimulated Raman loss or a stimulated Raman gain in accordance with the amplitude modulation as a result of the frequency difference between the first beam and the second beam resonating with the target molecule when the first applied beam and the second applied beam have been applied to a measurement position of an object, detects an interference pattern between the signal beam and the reference beam.

A second aspect of the present invention is an optical interferometer including: a light source that emits a coherent first beam and a second beam that has, with respect to the frequency of the first beam, a frequency difference corresponding to the natural frequency of a target molecule; amplitude modulating means that modulates the amplitude of the second beam; splitting means that splits the first beam into a reference beam and a first applied beam; frequency modulating means that modulates the frequency of the reference beam; optical path length adjusting means that adjusts the optical path length of the reference beam; and detecting means which, taking as a second applied beam the second beam whose amplitude has been modulated and taking as a signal beam the first beam that has experienced a stimulated Raman loss or a stimulated Raman gain in accordance with the amplitude modulation as a result of the frequency difference between the first beam and the second beam resonating with the target molecule when the first applied beam and the second applied beam have been applied to a measurement position of an object, detects an interference pattern between the signal beam and the reference beam whose frequency has been modulated.

A third aspect of the present invention is an optical interferometer including: a light source that emits a coherent first beam and a second beam that has, with respect to the frequency of the first beam, a frequency difference corresponding to the natural frequency of a target molecule; amplitude modulating means that modulates the amplitude of the second beam; splitting means that splits the first beam into a reference beam and a first applied beam; frequency modulating means that modulates the frequency of the first applied beam; optical path length adjusting means that adjusts the optical path length of the reference beam; and detecting means which, taking as a second applied beam the second beam whose amplitude has been modulated and taking as a signal beam the first beam that has experienced a stimulated Raman loss or a stimulated Raman gain in accordance with the amplitude modulation as a result of the frequency difference between the first beam and the second beam resonating with the target molecule when the first applied beam whose frequency has been modulated and the second applied beam have been applied to a measurement position of an object, detects an interference pattern between the signal beam and the reference beam.

A fourth aspect of the present invention is the optical interferometer of any of the first aspect to the third aspect, wherein in a case where the first applied beam is used as a pump beam and the second applied beam is used as a Stokes beam, the pump beam that has experienced a stimulated Raman loss in accordance with the amplitude modulation is used as the signal beam.

A fifth aspect of the present invention is the optical interferometer of any of the first aspect to the third aspect, wherein in a case where the first applied beam is used as a Stokes beam and the second applied beam is used as a pump beam, the Stokes beam that has experienced a stimulated Raman gain in accordance with the amplitude modulation is used as the signal beam.

A sixth aspect of the present invention is the optical interferometer of any of the first aspect to the fifth aspect, wherein the light source has a first laser that emits the first beam, a second laser that emits the second beam, and a synchronizing circuit that synchronizes the oscillation of the first laser and the oscillation of the second laser.

A seventh aspect of the present invention is the optical interferometer of any of the first aspect to the fifth aspect, wherein the light source has one laser and a wavelength conversion device that converts the wavelength of the beam emitted from the one laser to thereby generate the first beam and the second beam.

An eighth aspect of the present invention is the optical interferometer of any of the first aspect to the fifth aspect, wherein the light source has one laser, a wavelength conversion device that converts the wavelength of the beam emitted from the one laser to thereby generate two coherent beams with different wavelengths, and at least one wavelength conversion element that is disposed on the beam exiting side of the wavelength conversion device and converts the wavelength of at least one of the two coherent beams with different wavelengths.

A ninth aspect of the present invention is the optical interferometer of any of the first aspect to the fifth aspect, wherein the light source has one laser, splitting means that splits the beam emitted from the one laser into two beams, a first wavelength conversion device that converts the wavelength of one beam that has been split to thereby generate two coherent beams with different wavelengths, a second wavelength conversion device that converts the wavelength of the other beam that has been split to thereby generate two coherent beams with different frequencies, and selecting means that selects two coherent beams from among the four coherent beams generated by the first wavelength conversion device and the second wavelength conversion device.

A tenth aspect of the present invention is the optical interferometer of any of the first aspect to the fifth aspect, wherein the light source has a first laser, a second laser, a synchronizing circuit that synchronizes the oscillation of the first laser and the oscillation of the second laser, a first wavelength conversion device that converts the wavelength of the beam emitted from the first laser to thereby generate two coherent beams with different wavelengths, first selecting means that selects one coherent beam from among the two coherent beams generated by the first wavelength conversion device, a second wavelength conversion device that converts the wavelength of the beam emitted from the second laser to thereby generate two coherent beams with different wavelengths, and second selecting means that selects one coherent beam from among the two coherent beams generated by the second wavelength conversion device.

An eleventh aspect of the present invention is the optical interferometer of any of the first aspect to the fifth aspect, wherein the light source has one laser, splitting means that splits the beam emitted from the one laser into two beams, a first wavelength conversion device that converts the wavelength of one beam that has been split to thereby generate two coherent beams with different wavelengths, and selecting means that selects two coherent beams from among three coherent beams including the other beam that has been split and the two coherent beams generated by the first wavelength conversion device.

A twelfth aspect of the present invention is the optical interferometer of any of the first aspect to the eleventh aspect, further including measuring means that measures the change in the intensity of the second beam that has experienced a stimulated Raman loss or a stimulated Raman gain in accordance with the amplitude modulation.

A thirteenth aspect of the present invention is a data acquisition device including: a light source that emits a coherent first beam and a second beam that has, with respect to the frequency of the first beam, a frequency difference corresponding to the natural frequency of a target molecule; amplitude modulating means that modulates the amplitude of the second beam; splitting means that splits the first beam into a reference beam and a first applied beam; optical path length adjusting means that adjusts the optical path length of the reference beam; detecting means which, taking as a second applied beam the second beam whose amplitude has been modulated and taking as a signal beam the first beam that has experienced a stimulated Raman loss or a stimulated Raman gain in accordance with the amplitude modulation as a result of the frequency difference between the first beam and the second beam resonating with the target molecule when the first applied beam and the second applied beam have been applied to a measurement position of an object, detects an interference pattern between the signal beam and the reference beam; and first data acquiring means which, on the basis of the adjusted optical path length, the natural frequency of the target molecule, and the interference pattern detected by the detecting means, acquires phase data represented by the phase difference between the signal beam and the reference beam and molecule identification data identifying the molecular species.

A fourteenth aspect of the present invention is the data acquisition device of the thirteenth aspect, further including: scanning means that relatively moves the measurement position to thereby scan the object; and second data acquiring means which, on the basis of the phase data and the molecule identification data acquired at plural measurement positions as a result of the object being scanned by the scanning means, acquires image data representing a three-dimensional image or a tomographic image of the object in which a molecule identification function has been added to a phase interference image.

A fifteenth aspect of the present invention is a data acquisition method including: using a coherent first beam and a second beam that has, with respect to the frequency of the first beam, a frequency difference corresponding to the natural frequency of a target molecule; modulating the amplitude of the second beam to obtain a second applied beam; splitting the first beam into a reference beam and a first applied beam; adjusting the optical path length of the reference beam; detecting, taking as a signal beam the first beam that has experienced a stimulated Raman loss or a stimulated Raman gain in accordance with the amplitude modulation as a result of the frequency difference between the first beam and the second beam resonating with the target molecule when the first applied beam and the second applied beam have been applied to a measurement position of an object, an interference pattern between the signal beam and the reference beam; and, on the basis of the adjusted optical path length, the natural frequency of the target molecule, and the interference pattern detected by the detecting means, acquiring phase data represented by the phase difference between the signal beam and the reference beam and molecule identification data identifying the molecular species.

A sixteenth aspect of the present invention is the data acquisition method of the fifteenth aspect, further including: relatively moving the measurement position to thereby scan the object; and, on the basis of the phase data and the molecule identification data acquired at plural measurement positions, acquiring image data representing a three-dimensional image or a tomographic image of the object in which a molecule identification function has been added to the phase interference image.

Advantageous Effects of Invention

According to the present invention, the stimulated Raman scattering process can be utilized to obtain scattered beam phase data and molecule identification data identifying molecular species. Furthermore, according to the present invention, on the basis of the scattered beam phase data and the molecule identification data obtained utilizing the stimulated Raman scattering process, image data representing a three-dimensional image or a tomographic image of an object in which a molecule identification function has been added to a phase interference image can be acquired.

BRIEF DESCRIPTION OF DRAWINGS

FIG. 1 is a schematic diagram showing applied beams and scattered beams in the stimulated Raman scattering process;

FIG. 6A is an explanatory diagram describing the principle by which a phase interference image is acquired at a predetermined depth of an object by optical interferometric imaging;

FIG. 6B is a schematic diagram showing a phase difference between a signal beam and a reference beam;

FIG. 12 is a schematic diagram showing a third example modification of the light source;

DESCRIPTION OF EMBODIMENTS

Examples of embodiments of the present invention will be described in detail below with reference to the drawings.

<Stimulated Raman Scattering Beams>

First, stimulated Raman scattering will be briefly described.

Figure 2A:
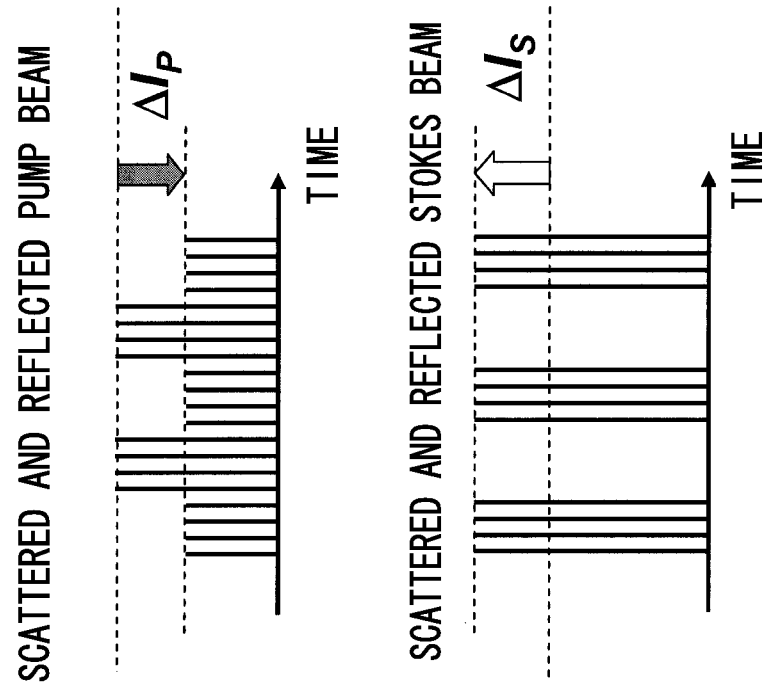
FIG. 2A is a schematic diagram showing a pump beam and a Stokes beam used in stimulated Raman scattering.
Figure 2B:
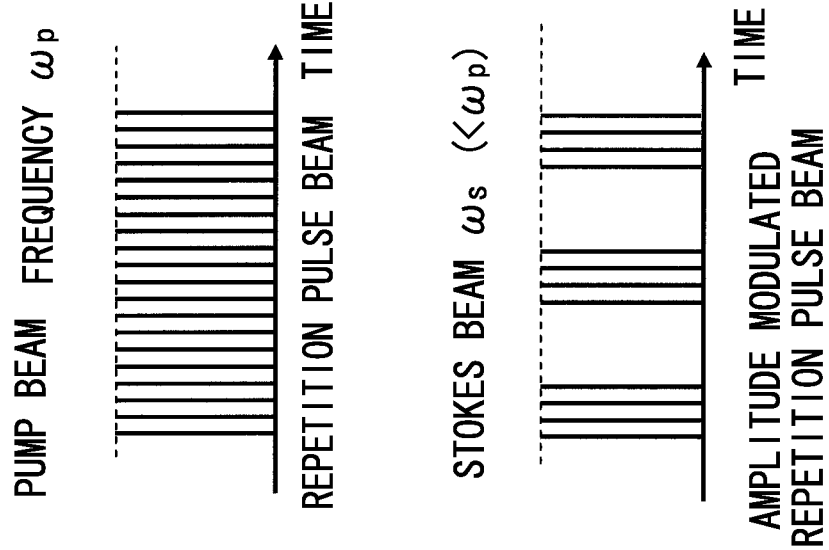
FIG. 2B is a schematic diagram describing the principle of using the stimulated Raman loss effect or the stimulated Raman scattering Raman gain effect to detect the stimulated Raman scattering process.

FIG. 1 is a schematic diagram showing applied beams and scattered beams in the stimulated Raman scattering (SRS) process. FIG. 2A is a schematic diagram showing a pump beam and a Stokes beam used in stimulated Raman scattering. In FIG. 2A, a case is shown where the Stokes beam is amplitude modulated, but as described later the pump beam may also be amplitude modulated. FIG. 2B is a schematic diagram describing the principle of using the stimulated Raman loss effect or the stimulated Raman gain effect to detect the stimulated Raman scattering process.

As shown in FIG. 1, in stimulated Raman scattering, a pump beam with frequency $\omega_p$ and a Stokes beam with frequency $\omega_s$ are simultaneously applied to a sample S. The frequency $\omega_s$ of the Stokes beam is smaller than the frequency $\omega_p$ of the pump beam. If the difference ($\omega_p-\omega_s$) between the frequencies of the pump beam and the Stokes beam matches the natural frequency $\Omega$ of a target molecule, beam scattering of the pump beam is induced by the stimulation process under an electric field in which the pump beam and the Stokes beam are superposed.

As shown in FIG. 2B, as a result of beam scattering being induced, the Stokes beam experiences an intensity gain $\Delta I_S$ called a stimulated Raman gain (SRG). Furthermore, the pump beam experiences an intensity loss Alp called a stimulated Raman loss (SRL). Below, the Stokes beam that has experienced the stimulated Raman gain will be called an SRG beam and the pump beam that has experienced the stimulated Raman loss will be called an SRL beam. When the pump beam and the Stokes beam are made incident on the sample S under given conditions, the SRG beam and the SRL beam exit from the sample S. The stimulated Raman scattering process occurs when the phases of the pump beam and the Stokes beam are aligned, that is, in a coherent state, so the SRG beam and the SRL beam both become coherent beams whose phases are aligned, and phase data of the pump beam and the Stokes beam is retained.

In the stimulated Raman scattering process, ordinarily the change in the intensity of the SRG beam or the SRL beam is detected as a signal. By varying the value of the frequency $\omega_s$ with respect to the value of the frequency $\omega_p$, the molecular species is identified in accordance with the natural frequency $\Omega$ of the molecule. In the present embodiment, the phase data of the SRG beam or the SRL beam is also detected by interference, but this will be described later.

Furthermore, the stimulated Raman scattering process occurs only if the frequency difference ($\omega_p-\omega_s$) matches the natural frequency $\Omega$ of the molecule. This phenomenon is called resonance. In other words, if a molecule with a natural frequency $\Omega$ matching the frequency difference ($\omega_p-\omega_s$) is not present, the stimulated Raman scattering process resulting from resonance will not occur. Consequently, the stimulated Raman scattering process has the advantage that background noise called a nonresonant background does not occur in the detection signal.

Here, the difference between a case where there is resonance and a case where there is no resonance will be described returning to FIG. 1. In the case where there is no resonance, only the pump beam and the Stokes beam transmitted through the sample S or reflected and scattered by the sample S are observed. In the case where there is resonance, the SRG beam and the SRL beam that have exited are observed in addition to the beams observed in the case where there is no resonance. Scattering in the case where there is no resonance is called Rayleigh scattering. In this way, different beams are observed in the case where there is resonance and in the case where there is no resonance.

Other known forms of Raman scattering include spontaneous Raman scattering and coherent anti-Stokes Raman scattering (CARS). In spontaneous Raman scattering, a coherent scattered beam is not obtained. And in CARS, the intensity of the detection signal is large compared to the intensity of the detection signal in stimulated Raman scattering, but the nonresonant background signal is also large and the signal-to-background noise ratio (S/B) is low. Stimulated Raman scattering, which does not produce a nonresonant background, has an extremely high S/B and a superior ability to identify molecular species compared to CARS.

As the pump beam and the Stokes beam, generally pulse laser beams that have a short pulse duration measured in picoseconds or femtoseconds and are repeatedly oscillated at a high frequency are used. However, in the present embodiment, the pump beam and the Stokes beam are not limited to pulse laser beams provided that they are beams that in principle produce the stimulated Raman scattering process. For example, as the pump beam or the Stokes beam, a beam emitted from a super luminescent diode (SLD), for example, may also be used. Furthermore, as the pump beam and the Stokes beam, continuously oscillated laser beams (CW beams) may also be used. Furthermore, in the present embodiment, of the pump beam and the Stokes beam, the beam that is unrelated to the generation of stimulated Raman scattering, and beams other than the portion of the reference beam that interferes when acquiring the phase interference image, may also be in a non-coherent state.

It suffices for the frequency difference ($\omega_p-\omega_s$) between the pump beam and the Stokes beam to become a specific value, and the wavelength region of the pump beam and the Stokes beam is arbitrary. The wavelength region of the pump beam and the Stokes beam is decided in accordance with the intended use. For example, for biological uses, near-infrared light, which is very safe and has a far reach into deep portions of living bodies, is used. Generally, near-infrared light is light with a wavelength of 800 nm to 2500 nm. For biological uses, near-infrared light in the wavelength range in which there is no water absorption is used. For example, there is the example using near-infrared light of 1375 nm or lower in optical coherence tomography (OCT) described later.

However, in stimulated Raman scattering, ordinarily the visible range of 800 nm or lower is often used for the wavelength region of the pump beam and the Stokes beam. The reason the wavelength region is limited is because if the wavelength of the pump beam becomes longer, the intensity of the scattered beam drops in proportion to the fourth power of the wavelength of the pump beam. The wavelength region usable in the optical interferometer pertaining to the present embodiment will be described later.

In FIG. 1, backscattering is shown where the SRG beam and the SRL beam exit the sample S in the opposite direction of the incident direction of the pump beam and the Stokes beam, but the SRG beam and the SRL beam are observed in various directions. The SRG beam (the Stokes beam that has experienced the stimulated Raman gain) and the SRL beam (the pump beam that has experienced the stimulated Raman loss) originating in the applied beams are observed in the directions in which the SRG beam or the SRL beam exits after being transmitted, reflected, scattered, or refracted.

Figure 3A:
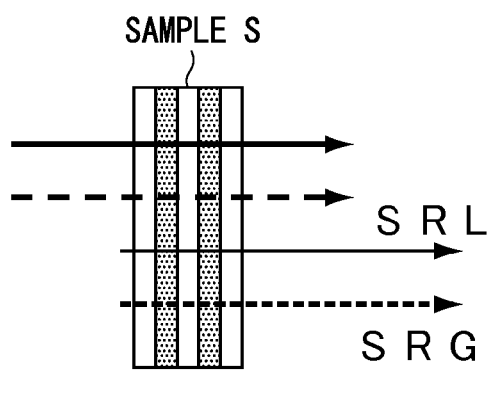
FIG. 3A is a schematic diagram showing an example where the direction in which stimulated Raman scattering is observed is a forward direction.
Figure 3B:
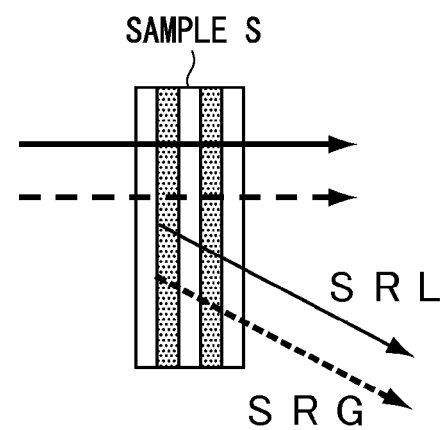
FIG. 3B is a schematic diagram showing an example where the direction in which stimulated Raman scattering is observed is a diagonal direction.
Figure 3C:
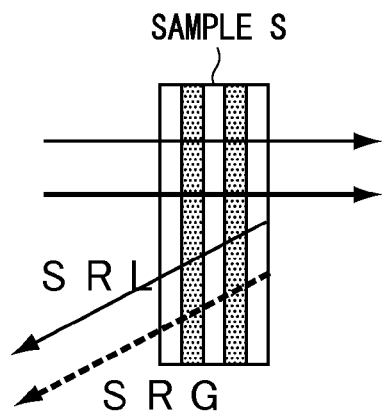
FIG. 3C is a schematic diagram showing an example where the direction in which stimulated Raman scattering is observed is a diagonal direction.
Figure 3D:
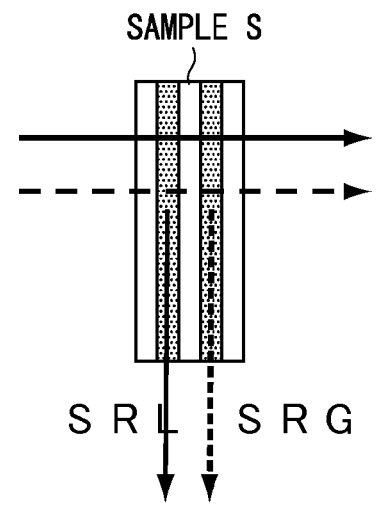
FIG. 3D is a schematic diagram showing an example where the direction in which stimulated Raman scattering is observed is a lateral direction.

FIG. 3A, FIG. 3B, FIG. 3C, and FIG. 3D are schematic diagrams showing other examples of directions in which the SRG beam or the SRL beam is observed. As shown in FIG. 3A, forward scattered beams and transmitted beams exiting in the same direction as the incident direction of the pump beam and the Stokes beam may also be observed. For example, in the case of a sample that transmits the applied beams, forward scattered beams are observed, and in the case of a sample that does not transmit the applied beams, backscattered beams are observed. Furthermore, as shown in FIG. 3B and FIG. 3C, beams that exit in a diagonal direction with respect to the incident direction of the pump beam and the Stokes beam after being reflected, scattered, or refracted due to the internal structure of the sample S may also be observed. Or, as shown in FIG. 3D, beams that exit in a lateral direction from the sample S may also be observed.

Furthermore, in FIG. 1, an example is shown where the pump beam and the Stokes beam are made incident coaxially with respect to the sample S, but the pump beam and the Stokes beam are not limited to coaxial incidence. It suffices provided that the pump beam and the Stokes beam are superposed at a desired position in the sample S, and the pump beam and the Stokes beam may also be made incident from opposite sides with respect to the sample S. Furthermore, the pump beam and the Stokes beam may also be made incident in such a way that the optical axis of the pump beam and the optical axis of the Stokes beam intersect one another inside the sample S. This kind of non-coaxial incident optical system is called an off-axis optical system. An off-axis optical system will be described later.

Optical Interferometer

First Embodiment

Next, an optical interferometer utilizing the stimulated Raman scattering process will be described.

(Example Configuration of Optical Interferometer)

First, the configuration of an optical interferometer will be described.

Figure 4:
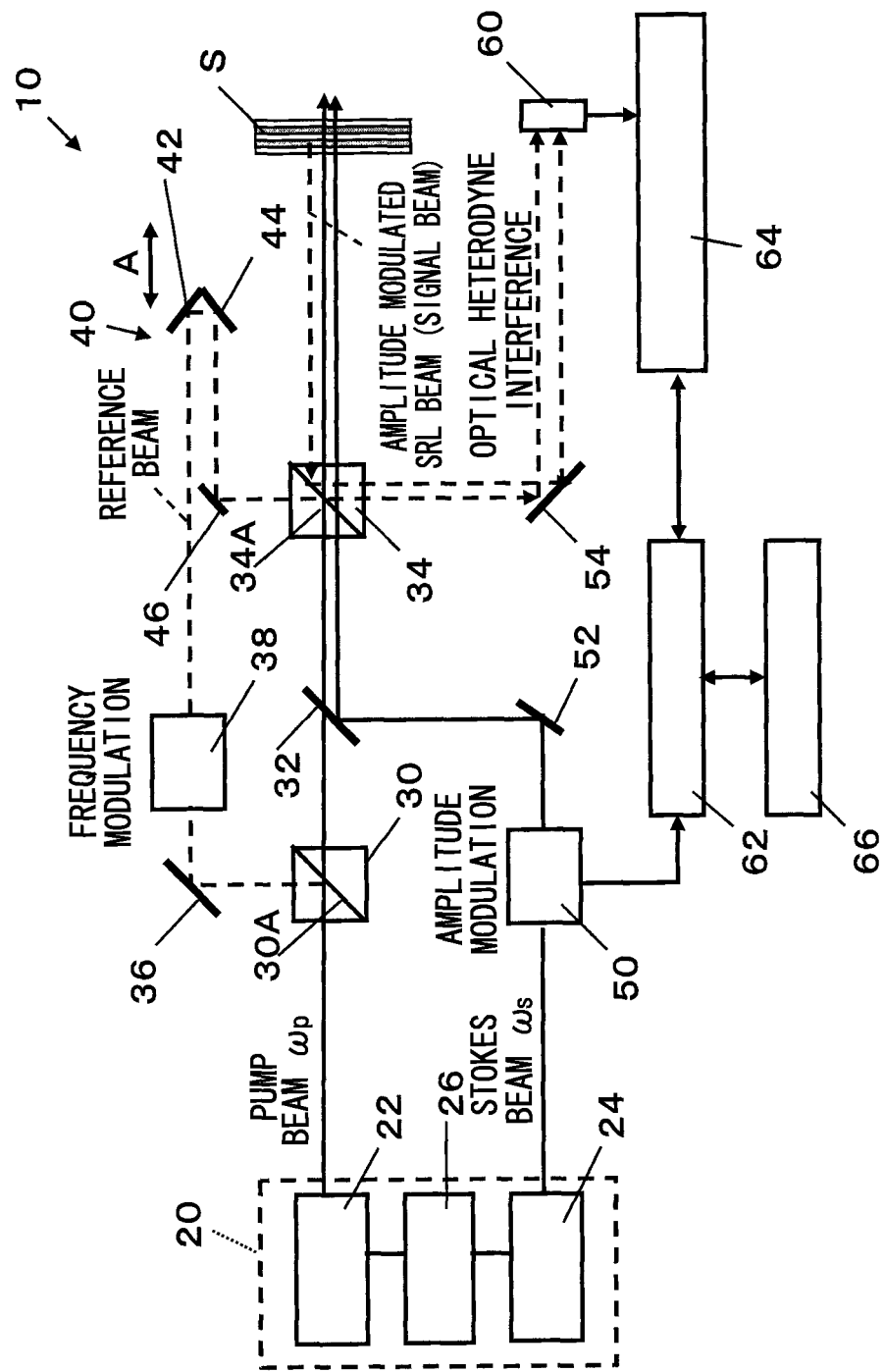
FIG. 4 is a schematic diagram showing an example of the configuration of an optical interferometer pertaining to an embodiment of the present invention.

FIG. 4 is a schematic diagram showing an example of the configuration of an optical interferometer pertaining to a first embodiment of the present invention. As shown in FIG. 4, an optical interferometer 10 is equipped with a light source 20 that emits two types of laser beams with different frequencies. The light source 20 is equipped with a laser 22 that emits a laser beam with frequency $\omega_p$ used as a pump beam, a laser 24 that emits a laser beam with frequency $\omega_s$ used as a Stokes beam, and a synchronizing circuit 26 that synchronizes the oscillation of the laser 22 and the oscillation of the laser 24. In the present embodiment, an example is described where pulse lasers that have a short pulse duration measured in picoseconds or femtoseconds and can be repeatedly oscillated at a high frequency are used as the laser 22 and the laser 24.

A beam splitter 30 that has a reflecting surface 30A is disposed on the beam exiting side of the laser 22. The laser beam with frequency $\omega_p$ emitted from the laser 22 is made incident on the beam splitter 30. The beam splitter 30 uses the reflecting surface 30A to transmit some of the incident beam and reflect the rest of the incident beam. Here, the beam transmitted through the beam splitter 30 is used as a pump beam and the beam reflected by the beam splitter 30 is used as a reference beam. The use of the beam splitter 30 is not limited to this splitting method, and it is also possible for the transmitted beam to be used as a reference beam and for the reflected beam to be used as a pump beam.

A selectively reflecting mirror 32 and a beam splitter 34 that has a reflecting surface 34A are disposed in this order from the beam splitter 30 side on the beam transmitting side of the beam splitter 30, that is, on the optical path of the pump beam. The selectively reflecting mirror 32 transmits the laser beam with frequency $\omega_p$ and reflects the laser beam with frequency $\omega_s$. As the selectively reflecting mirror 32, a mirror having the property of reflecting the laser beam with frequency $\omega_p$ and transmitting the laser beam with frequency $\omega_s$ may also be used. As the selectively reflecting mirror 32, generally a dichroic mirror, for example, is used. The beam splitter 34 transmits some or all of the beams made incident from one side (the left side and the upper side in FIG. 4) of the reflecting surface 34A and reflects some or all of the beams made incident from the other side (the right side and the lower side in FIG. 4) of the reflecting surface 34A. As the beam splitter 34, generally a half mirror, a beam splitter, or a polarizing beam splitter, for example, is used.

A reflecting mirror 36, a frequency modulation element 38, an optical delay device 40, and a reflecting mirror 46 are disposed in this order from the beam splitter 30 side on the beam reflecting side of the beam splitter 30, that is, on the optical axis of the reference beam. The frequency modulation element 38 is a modulation element that modulates the frequency of the incident beam. As the frequency modulation element 38, an acousto-optic modulator (AO or AOM) such as an acousto-optic deflector (AOD) or an electro-optic modulator (EOM) such as a Pockels cell, for example, is used.

The optical delay device 40 is equipped with a pair of reflecting mirrors 42 and 44 and a mirror driver (not shown in the drawings) such as a piezo element that moves the pair of reflecting mirrors 42 and 44 in the direction of arrow A. The pair of reflecting mirrors 42 and 44 fold back the optical path of the reference beam made incident from the frequency modulation element 38 to thereby apply the reference beam to the reflecting mirror 46. When the pair of reflecting mirrors 42 and 44 move, the optical path length of the reference beam is adjusted.

The phase difference between a later-described signal beam and the reference beam is set as a result of the optical path length of the reference beam (that is, the timing of temporal overlap between a signal pulse beam and a reference pulse beam, and moreover the phase difference of the reference pulse beam with respect to the signal pulse beam) being adjusted. Although it is not shown in the drawings, by using an appropriate optical element to further shorten the pulse duration of the reference beam and thereby further shorten the portion temporally overlapping the signal beam, the place of measurement can be further limited to increase the spatial resolution. This will be described later.

An amplitude modulation element 50, a reflecting mirror 52, the selectively reflecting mirror 32, and the beam splitter 34 are disposed in this order from the laser 24 side on the beam exiting side of the laser 24, that is, on the optical path of the Stokes beam. The laser beam (Stokes beam) with frequency $\omega_s$ emitted from the laser 24 is made incident on the amplitude modulation element 50. The amplitude modulation element 50 is a modulation element that modulates the amplitude of the incident beam. As the amplitude modulation element 50, an acousto-optic modulator such as an AOD or an electro-optic modulator such as a Pockels cell, for example, is used.

The beam splitter 34 transmits some or all of the pump beam and the Stokes beam that are made incident from the selectively reflecting mirror 32 and some or all of the reference beam made incident from the reflecting mirror 46. A sample S that is a measurement object is disposed on the pump beam exiting side of the beam splitter 34. A selectively reflecting mirror 54 such as a dichroic mirror and a photodetector 60 are disposed in this order from the beam splitter 34 side on the reference beam exiting side of the beam splitter 34. The photodetector 60 is not particularly limited provided that it is a photodetector that is sensitive to the signal beam and the reference beam and has a sufficient response characteristic with respect to the frequency band to be measured. As the photodetector 60, a light receiving element such as a photodiode (PD) or a charge-coupled device (CCD), for example, is used.

A signal processor 64 such as a high speed sampler is electrically connected to the photodetector 60. The signal processor 64 is electrically connected to an analyzer 62. As the analyzer 62, generally a lock-in amplifier or a FFT analyzer, for example, is used. Furthermore, the analyzer 62 is electrically connected to the amplitude modulation element 50. Moreover, the analyzer 62 is electrically connected to a data processor 66 that performs various types of data processing, such as image data acquisition processing, on the basis of obtained data. Here, "electrically connected" means capable of transmitting and receiving electrical signals.

A lock-in amplifier is an amplifier that has both an amplifying (amp) function and a specific signal detecting (lock-in) function. Furthermore, a FFT analyzer is an analyzer that digitally (discretely) samples an input signal waveform, Fourier transforms the sampled data using the fast Fourier transform (FFT), and displays the results of the Fourier transform.

Furthermore, the data processor 66 is configured as a computer that performs control of the device overall and various operations. That is, the data processor 66 is equipped with a central processing unit (CPU), a read-only memory (ROM) in which various programs are stored, a random access memory (RAM) that is used as a work area when the programs are executed, a nonvolatile memory that stores various types of data, and an input/output interface (I/O). The CPU, the ROM, the RAM, the nonvolatile memory, and the I/O are interconnected via a bus.

Furthermore, although it is not shown in the drawings, a scanning mechanism that scans the sample S that is the measurement object is disposed in the optical interferometer 10. The optical interferometer 10 uses the scanning mechanism to relatively move the measurement position and scan the sample S to thereby acquire measurement results at plural measurement positions.

(General Actions of Optical Interferometer)

Next, the actions of the optical interferometer will be briefly described.

In the optical interferometer 10, the laser 22 and the laser 24 are synchronized and oscillate, the laser beam with frequency $\omega_p$ is emitted from the laser 22, and the laser beam with frequency $\omega_s$ is emitted from the laser 24. The laser beam with frequency $\omega_p$ emitted from the laser 22 is made incident on the beam splitter 30 and is split into the reference beam and the pump beam by the beam splitter 30.

The laser beam (pump beam) with frequency $\omega_p$ transmitted through the reflecting surface 30A of the beam splitter 30 is transmitted through the selectively reflecting mirror 32, is transmitted through the reflecting surface 34A of the beam splitter 34, and is applied to the sample S. The laser beam (Stokes beam) with frequency $\omega_s$ emitted from the laser 24 has its amplitude modulated by the amplitude modulation element 50. The amplitude modulated Stokes beam has its optical path bent by the reflecting mirror 52, is reflected by the selectively reflecting mirror 32, and is made incident on the beam splitter 34. The amplitude modulated Stokes beam is transmitted through the reflecting surface 34A of the beam splitter 34 and is applied to the sample S. In the present embodiment, the pump beam and the Stokes beam are applied to the sample S coaxially by the selectively reflecting mirror 32 and the beam splitter 34.

When the pump beam and the Stokes beam are applied to the sample S, the SRG beam and the SRL beam exit from the sample S. In FIG. 4, the pump beam and the Stokes beam are depicted by solid lines and the SRG beam and the SRL beam are depicted by dashed lines. However, in FIG. 4, only the SRL beam is shown. The SRG beam and the SRL beam are amplitude modulated like the Stokes beam. The SRG beam and the SRL beam are reflected by the reflecting surface 34A of the beam splitter 34 and are made incident on the selectively reflecting mirror 54. The selectively reflecting mirror 54 transmits the SRG beam with frequency $\omega_s$ and reflects the SRL beam with frequency $\omega_p$. The amplitude modulated SRL beam is reflected by the selectively reflecting mirror 54 and is applied to the photodetector 60 as a signal beam.

The laser beam (reference beam) with frequency $\omega_p$ reflected by the reflecting surface 30A of the beam splitter 30 has its optical path bent by the reflecting mirror 36 and is made incident on the frequency modulation element 38. The reference beam made incident on the frequency modulation element 38 has its frequency modulated (that is, has its frequency shifted), has its optical path length adjusted by the optical delay device 40, has its optical path bent by the reflecting mirror 46, and is made incident on the beam splitter 34. The reference beam whose frequency has been modulated and whose temporal overlap and phase difference with the signal beam have been adjusted is transmitted through the reflecting surface 34A of the beam splitter 34, is reflected by the selectively reflecting mirror 54, and is applied to the photodetector 60.

In the present embodiment, the amplitude modulated SRL beam (signal beam) and the reference beam whose frequency has been modulated and whose phase difference with respect to the signal beam has been adjusted undergo optical heterodyne interference. This optical heterodyne interference will be described later. The interference pattern between the signal beam and the reference beam is detected by the photodetector 60. The detection signal of the photodetector 60 is input to the signal processor 64. The signal processor 64 performs processing such as amplification and wavelength filtering on the input signal and outputs the processed signal to the analyzer 62.

The analyzer 62 identifies the modulation frequency of the amplitude modulation element 50 and selectively detects the signal modulated at the identified frequency from the signal input from the signal processor 64. The analyzer 62 outputs the selectively detected signal as an output signal of the optical interferometer. The output signal will be described later. Furthermore, as described later, the data processor 66 creates a phase interference image having species and distribution information of a target molecule based on the stimulated Raman scattering beam (the SRL beam or the SRG beam) and acquires image data representing a three-dimensional image or a tomographic image of an object in which a molecule identification function has been added to a phase interference image of only a conventional shape.

Here, the actions of the optical interferometer 10 will be more conceptually described.

Figure 5:
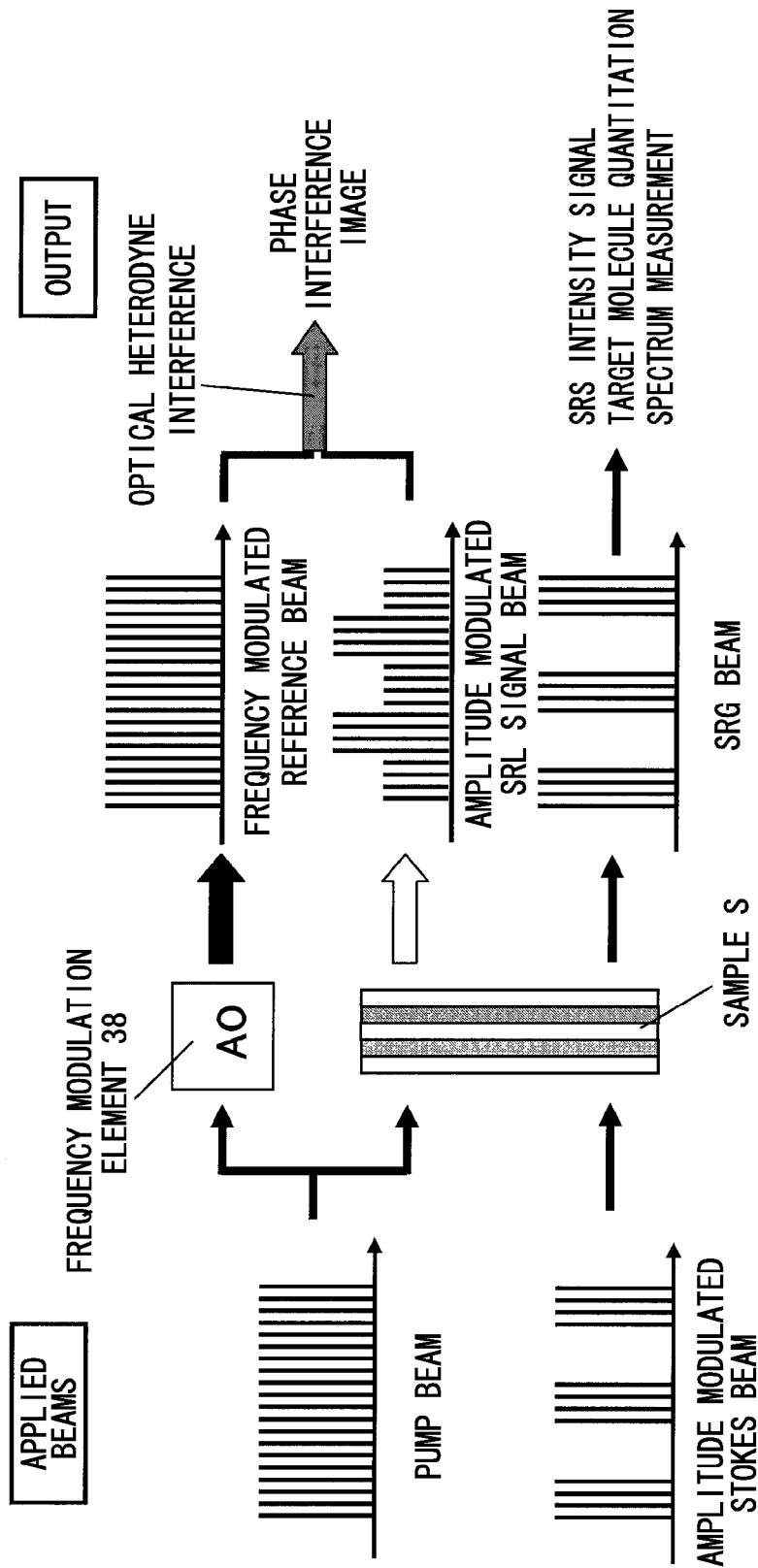
FIG. 5 is a conceptual diagram showing the actions of the optical interferometer shown in FIG. 4.

FIG. 5 is a conceptual diagram showing the actions of the optical interferometer shown in FIG. 4. As shown in FIG. 5, in the present embodiment, the laser beam (pump beam) with frequency $\omega_p$ emitted from the laser 22 is split into the reference beam and the pump beam that is applied to the sample S. The reference beam is frequency modulated by the frequency modulation element 38. Furthermore, the Stokes beam amplitude modulated by the amplitude modulation element 50 is generated from the laser beam (Stokes beam) with frequency $\omega_s$ emitted from the laser 24. The pump beam and the amplitude modulated Stokes beam are applied to the sample S, whereby the SRG beam and the SRL beam that have been amplitude modulated like the Stokes beam are obtained.

In the present embodiment, the SRL beam, which is the pump beam that has experienced the stimulated Raman loss, is selected as the signal beam. The SRL beam is a beam that has been split from the laser beam with frequency $\omega_p$ generated by the same laser 22 as the reference beam, and is coherent with the reference beam. Consequently, the amplitude modulated SRL beam (signal beam) and the frequency modulated reference beam undergo optical heterodyne interference. Because a beam emitted from the same light source is split into the signal beam and the reference beam, phase fluctuations in the interference pattern of these are reduced. The stimulated Raman gain $\Delta I_S$ can also be obtained from the amplitude modulated SRG beam not used in the interference. The stimulated Raman gain $\Delta I_S$ increases in proportion to the number of molecules resonating at the natural frequency $\Omega$. For this reason, the stimulated Raman gain $\Delta I_S$ obtained by observing the SRG beam may also be used as molecule quantitation data.

(Optical Heterodyne Interference)

Here, the principle of using optical heterodyne interference to amplify the signal intensity will be described.

The change in the intensity of the SRG beam and the change in the intensity of the SRL beam obtained by the stimulated Raman scattering process are both faint. By undergoing optical heterodyne interference, the change in the intensity of the SRL beam used as the signal beam becomes amplified.

Let $E_{s0}$ denote the largest amplitude of the electric field of the signal beam, F denote the frequency of the signal beam, and $\theta_s(x)$ denote the phase of the signal beam. Furthermore, let $E_{r0}$ denote the largest amplitude of the electric field of the reference beam, F+f denote the frequency of the reference beam after modulation, and $\theta_r(x)$ denote the phase of the reference beam. Electric field intensities $E_s$ and $E_r$ of the signal beam and the reference beam are given by the following equations.

$$E_s = E_s \cos[2\pi Ft + \theta_s(x)] \text{(Signal Beam)}$$

$$E_r = E_r \cos[2\pi(F+f)t + \theta_r(x)] \text{(Reference Beam)} \quad \text{[Equations 1]}$$

Furthermore, intensity I of the interference pattern after optical heterodyne interference is given by the following equation.

$$I = |E_s + E_r|^2 = E_s^2 + E_r^2 + 2E_{s0}E_{r0}\cos[2\pi ft + (\theta_s(x) - \theta_r(x))] \quad \text{[Equation 2]}$$

The following three things are understood from the third term in the above equation.

First, it will be understood that, because of optical heterodyne interference, a beat signal having a frequency f is newly generated. If, for example, the reference beam is frequency modulated and the frequency F of the signal beam is set to 1000 Hz and the frequency (F+f) of the reference beam is set to 1005 Hz, a beat signal with a frequency of 5 Hz is generated. By using a synchronous detector, for example, to sort out and detect the beat signal, measurement can be performed at a high S/B.

Furthermore, even if the largest electric field amplitude $E_{s0}$ of the signal beam is small, by increasing the largest electric field amplitude $E_{r0}$ of the reference beam, the intensity of the interference pattern observed as the beat signal with the frequency f is amplified to a power of the electric field amplitude of the reference beam. For example, by setting the largest electric field amplitude $E_{r0}$ to 10,000 times larger than the largest electric field amplitude $E_{s0}$ of the signal beam, the slight change in the amplitude of the stimulated Raman loss or stimulated Raman gain of the signal beam can in principle be amplified to 10,000 times or more.

Moreover, the phase difference $(\theta_s(x) - \theta_r(x))$ between the signal beam and the reference beam is recorded as phase data. Because of this, position data of the molecule of the signal source becomes recorded with good precision. The recording of the position data will be described next.

Here, the wavelength region usable in the optical interferometer pertaining to the present embodiment will be described.

As mentioned above, in stimulated Raman scattering, when the wavelength of the pump beam becomes longer, the intensity of the scattered beam drops, so the wavelength region of the pump beam and the Stokes beam is limited. However, in the present embodiment, the intensity of the interference pattern is amplified to a power of the electric field amplitude of the reference beam by optical heterodyne interference, so the limit on the wavelength region of the pump beam and the Stokes beam is mitigated. For example, it is also possible to set the wavelength region of the pump beam and the Stokes beam to 1000 nm or higher. By lengthening the wavelength of the pump beam, the measurement range in the depth direction expands.

(Optical Interferometric Imaging)

In conventional optical interferometric imaging such as optical coherence tomography (OCT), phase data is recorded by the interference between the reflected beam or Rayleigh scattered beam and the reference beam. In contrast, in the present embodiment, phase data is recorded by the interference between the SRG beam or SRL beam obtained by stimulated Raman scattering and the reference beam. In the present embodiment, the phase data can be recorded by changing the frequency of the Stokes beam in accordance with the natural frequency of the target molecule (that is, per molecular species) and acquiring the signal resulting from interference.

For example, in a case where the wavelength of the pump beam is fixed, by sweeping the wavelength of the Stokes beam at a high speed, the stimulated Raman scattering effect of various wavelengths may also be detected at a high speed. Furthermore, the stimulated Raman scattering effect of various wavelengths may also be detected at one time using a beam including at one time a wavelength in the measurement wavelength range. At this time, the wavelength of the Stokes beam may be fixed and the wavelength of the pump beam may be swept at a high speed, or a beam including at one time a wavelength in the measurement wavelength range may also be used as the pump beam. Both methods may be methods which, by also sweeping the wavelength of the reference beam at a high speed or using a reference beam including at one time a wavelength in the measurement wavelength range, perform the detection of the stimulated Raman scattering effect of various wavelengths at one time in regard to the depth direction.

As the wavelength sweeping method, the same methods as those used in conventional optical interferometric imaging, such as swept-source OCT (SS-OCT) and spectral-domain OCT (SD-OCT), can be used.

The principle of phase data recording is the same as in conventional optical interferometric imaging.

FIG. 6A is an explanatory diagram describing the principle by which a phase interference image is acquired at a predetermined depth of an object by optical interferometric imaging. FIG. 6B is a schematic diagram showing the phase difference between the signal beam and the reference beam. As shown in FIG. 6A, in a case where the signal beam is obtained by reflection from a sample having a layered structure inside, this gives rise to a time and phase delay proportional to depth the deeper the beam is reflected from deep portions. In optical interferometric imaging, as shown in FIG. 6B, the optical path length of the reference beam is changed (that is, the optical path length is swept) to adjust the temporal overlap between the signal beam and the reference beam and to adjust the phase difference. In the present embodiment, the optical delay device 40 can adjust the temporal overlap between the signal beam and the reference beam and adjust the phase difference.

The principle of phase interference image acquisition described above is the same as the principle of signal acquisition in time-domain OCT (TD-OCT). In the acquisition of the phase interference image, the phase interference image in the depth direction can be constructed without a sweep of the optical path length by combining the aforementioned SS-OCT method or SD-OCT method that are frequency sweeping methods with respect to the signal beam and the reference beam.

The measurement resolution in the depth direction can also be increased by limiting the coherent temporal overlap with the signal beam by shortening the pulse time duration of the reference beam or the duration in which the phase is held. In FIG. 6A, a state in which the signal beam and the reference beam temporally overlap is schematically depicted.

In a case where, in the temporal overlap between the signal beam and the reference beam, the phase difference between them is zero, the signal beam and the reference beam reinforce one another the most. Consequently, by temporally superposing the reflection beam (signal beam) from a predetermined depth and the reference beam and making their phase difference zero, the reflection beam from the predetermined depth is amplified the most. Because of this, a phase interference image in the depth direction of the sample can be acquired with the precision of the phase difference measurement. Generally the precision of conventional phase difference measurement reaches 0.1° or higher, and in principle it becomes possible to discern irregularities of about 1 nm with a beam with a wavelength of 1000 nm, for example.

(Characteristics of Output Signal)

Next, the output signal of the optical interferometer will be described.

Figure 7A:
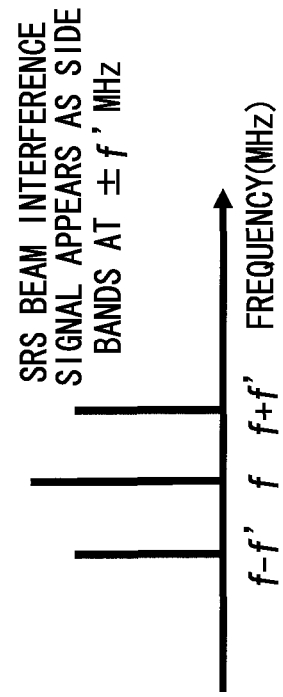
FIG. 7A is a schematic diagram showing an output signal, in the time domain when there is resonance, of the optical interferometer shown in FIG. 4.

FIG. 7A, FIG. 7B, FIG. 7C, and FIG. 7D are schematic diagrams showing the output signal of the optical interferometer shown in FIG. 4. As shown in FIG. 7A, when the SRL beam (signal beam) that has been amplitude modulated and the reference beam that has been frequency modulated by frequency f undergo optical heterodyne interference, in a case where the SRL beam is being obtained by resonance with the molecule, an amplitude modulated interference signal (interferogram) is detected when seen in the time domain.

Figure 7B:
FIG. 7B is a schematic diagram showing the output signal, in the frequency domain when there is resonance, of the optical interferometer shown in FIG. 4.
Figure 7C:
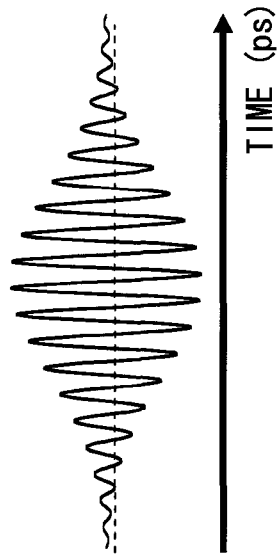
FIG. 7C is a schematic diagram showing the output signal, in the time domain when there is no resonance, of the optical interferometer shown in FIG. 4.
Figure 7D:
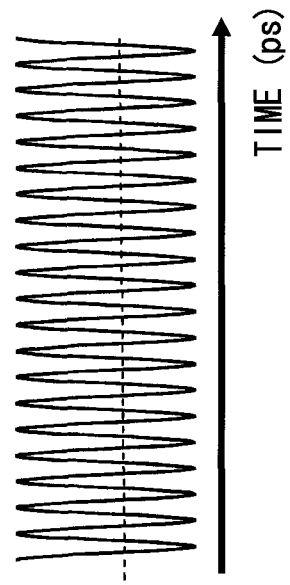
FIG. 7D is a schematic diagram showing the output signal, in the frequency domain when there is no resonance, of the optical interferometer shown in FIG. 4.

As shown in FIG. 7B, when the amplitude modulated interference signal is seen in the frequency domain, side bands originating in the SRL beam appear on both sides of the beat frequency f. For example, in a case where the beat frequency f is 30 MHz and the modulation frequency of the amplitude modulation is 3 MHz, the side bands appear in positions ±3 MHz from the beat frequency f, that is, at 27 MHz and 33 MHz. In a case where the target molecule is not present in the predetermined measurement position and resonance does not occur, as shown in FIG. 7C, the amplitude of the interference signal becomes constant. In this case, as shown in FIG. 7D, when seen in the frequency domain, only the band of the beat frequency f is measured and the side bands are not measured.

If the electric field amplitude of the amplitude modulated signal beam is changed to $E_s'$ and the largest electric field amplitude is changed to $E_{s0}'$, the intensity I of the interference pattern after optical heterodyne interference is rewritten to the following equation.

$$I = |E_s' + E_r|^2 = E_s'^2 + E_r^2 + 2E_{s0}'E_{r0} \cos[2\pi ft + (\theta_s(x) - \theta_r(x))]$$ [Equation 3]

The largest electric field amplitude $E_{s0}'$ of the signal beam fluctuates due to amplitude modulation. As will be understood from the above equation, in a case where the SRL beam is being obtained by resonance with the molecule, the amplitude of the beat signal is also periodically modulated. For example, in the case of measuring the distribution of molecules having a natural frequency at 1600 cm$^{-1}$, the frequency difference ($\omega_p - \omega_s$) between the pump beam and the Stokes beam is set to 1600 cm$^{-1}$ and whether or not there is periodic modulation of the amplitude of the beat signal is observed. If periodic modulation of the amplitude of the beat signal is observed, the target molecule is present in the measurement position and the SRL beam is obtained by resonance with the target molecule. If periodic modulation of the amplitude of the beat signal is not observed, the target molecule is not present in the measurement position.

As described above, in the present embodiment, the measurement position is relatively moved and the object is scanned. The case where the target molecule is present in the measurement position and the case where the target molecule is not present in the measurement position are discriminated by whether or not there is modulation in the amplitude of the optical interference signal or whether or not there are side bands in the Fourier transformed spectrum. In a case where the target molecule is present, its amplitude intensity is proportional to the Raman scattering cross section of the vibrational mode that gives the natural frequency and the concentration of the target molecule. By sweeping the frequency of the Stokes beam and by scanning the object, molecule identification data (target molecular species and quantity) at plural measurement positions and data representing the spatial distribution thereof is acquired.

On the basis of the molecule identification data and the phase difference data of the signal beam and reference beam, a phase interference image having species and spatial distribution data of the target molecule is acquired, and image data representing a three-dimensional image or a tomographic image of the object in which a molecule identification function has been added to the phase interference image is acquired. These data processes are performed by the data processor 66 shown in FIG. 4.

When just the pump beam with frequency $\omega_p$ is applied to the sample S while spatially scanning it and a phase interference image of the reference beam and a reflection beam or Rayleigh scattered beam of the object is acquired beforehand, data of only the shape of the object is obtained. By synthesizing and comparing molecule identifying phase interference images of the stimulated Raman scattering beam and the reference beam, an analysis of the spatial distribution and abundance of the target molecule with respect to the shape of the object can be performed.

Second Embodiment

Next, an optical interferometer pertaining to a second embodiment will be described.

Figure 8:
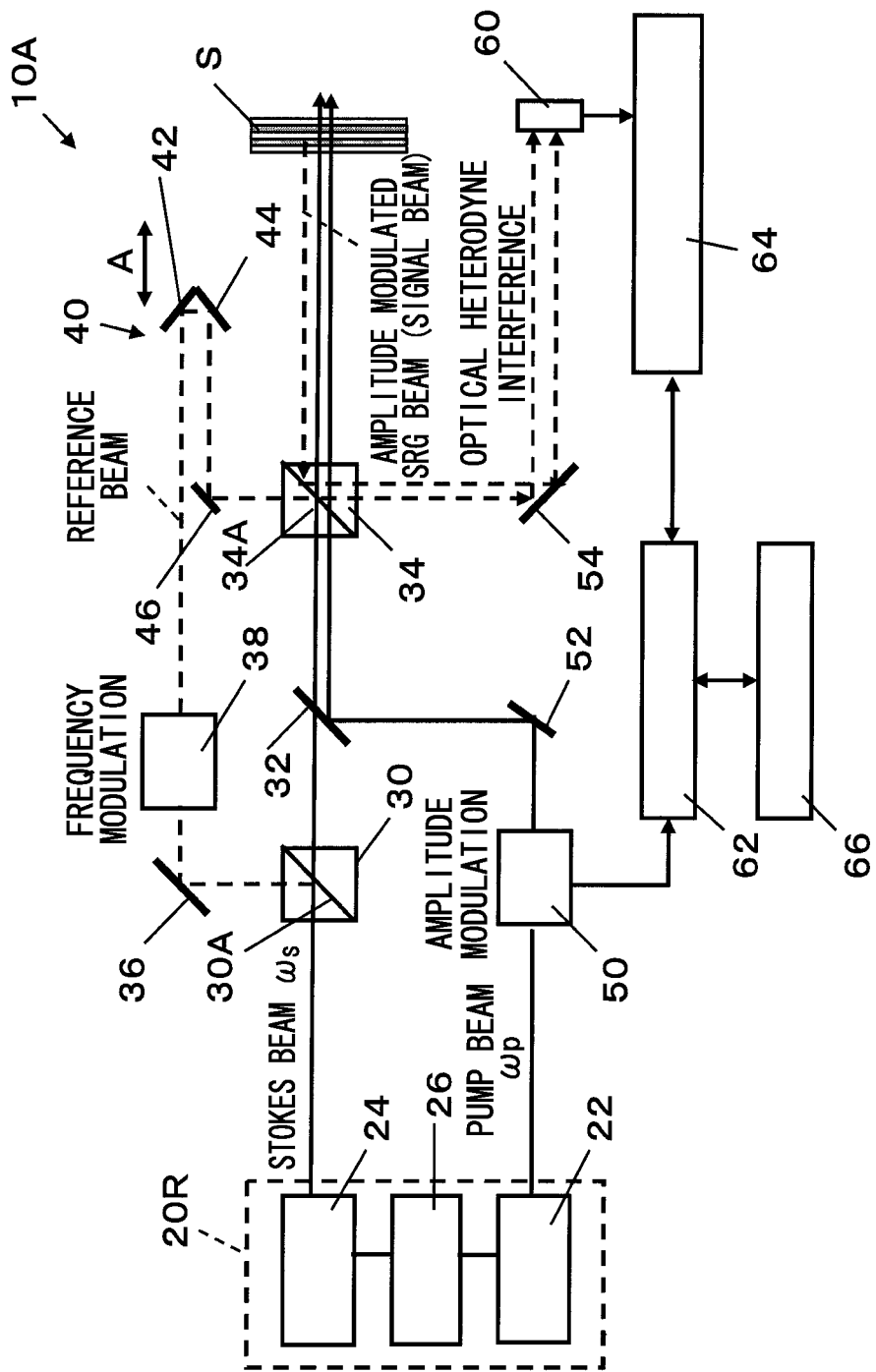
FIG. 8 is a schematic diagram showing an example of the configuration of an optical interferometer pertaining to a second embodiment of the present invention.

FIG. 8 is a schematic diagram showing an example of the configuration of the optical interferometer pertaining to the second embodiment of the present invention. An optical interferometer 10A pertaining to the second embodiment has the same configurations as those of the first embodiment except that it is configured in such a way that the pump beam and the Stokes beam are inverted, so the same reference signs are assigned to the same constituent parts and description will be omitted.

In the optical interferometer 10A, the positions of the laser 22 and the laser 24 are reversed, and the laser beam with frequency $\omega_s$ emitted from the laser 24 is made incident on the beam splitter 30 and split into the reference beam and the Stokes beam by the beam splitter 30. Furthermore, the laser beam with frequency $\omega_p$ emitted from the laser 22 is made incident on the amplitude modulation element 50 and has its amplitude modulated by the amplitude modulation element 50.

Figure 9:
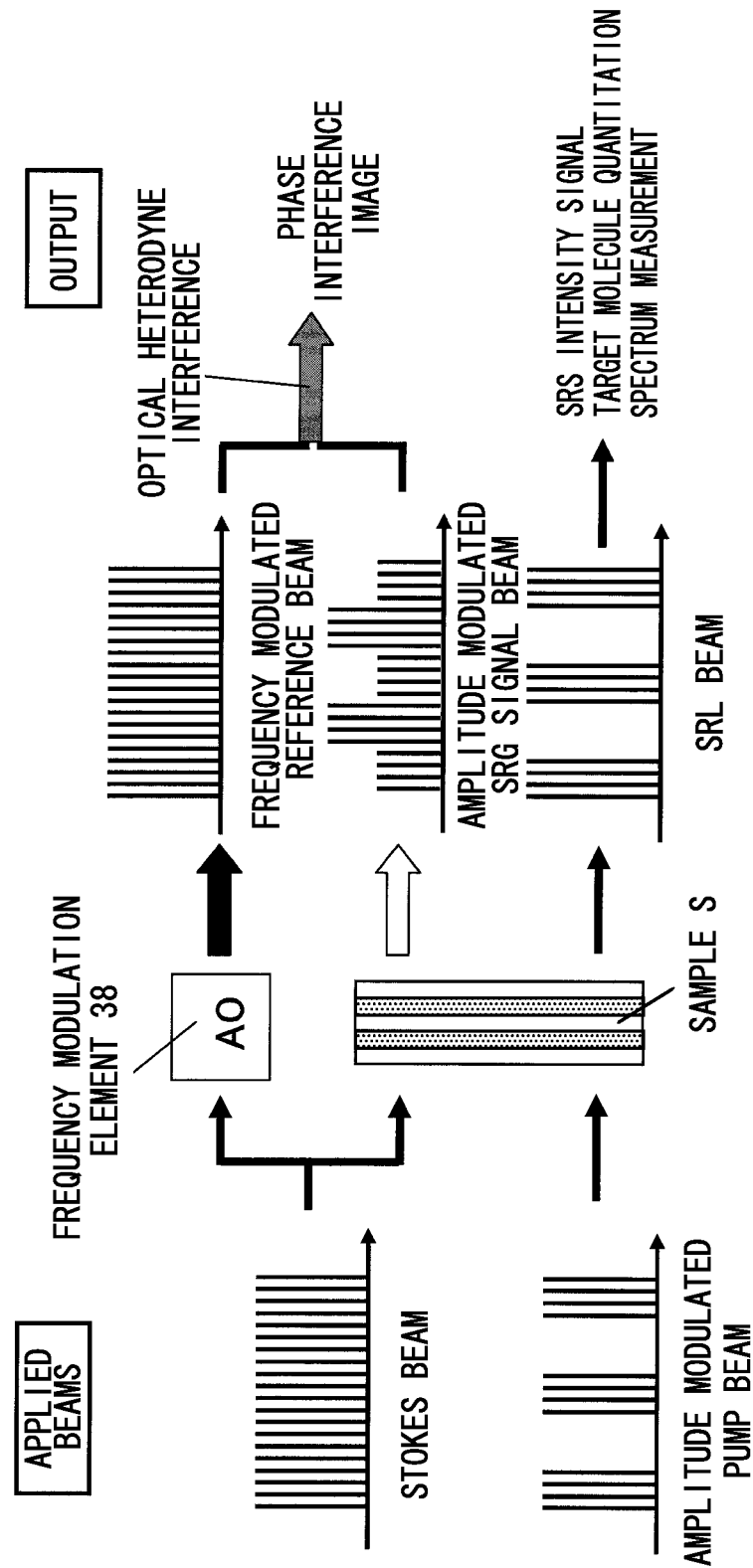
FIG. 9 is a conceptual diagram showing the actions of the optical interferometer shown in FIG. 8.

FIG. 9 is a conceptual diagram showing the actions of the optical interferometer shown in FIG. 8.

As shown in FIG. 9, in the present embodiment, the laser beam (Stokes beam) with frequency $\omega_s$ emitted from the laser 24 is split into the reference beam and the Stokes beam that is applied to the sample S. The reference beam is frequency modulated by the frequency modulation element 38. Furthermore, the amplitude modulated pump beam is generated from the laser beam (pump beam) with frequency $\omega_p$ emitted from the laser 22. The amplitude modulated pump beam and the Stokes beam are applied to the sample S, whereby the SRG beam and the SRL beam that have been amplitude modulated like the pump beam are obtained.

Here, the SRG beam, which is the Stokes beam that has experienced the stimulated Raman gain, is selected as the signal beam. The SRG beam is a beam that has been split from the laser beam with frequency $\omega_s$ generated by the same laser 24 as the reference beam, and is coherent with the reference beam. Consequently, the amplitude modulated SRG beam (signal beam) and the frequency modulated reference beam undergo optical heterodyne interference. Because of this, phase fluctuations in the interference pattern are reduced. Like in the first embodiment, the amplitude modulated SRL beam not used in the interference may also be used for molecule quantitation.

<Example Modifications of Light Source>

In the first and second embodiments, examples were described which used a light source equipped with two lasers and a synchronizing circuit that synchronizes the oscillation of the two lasers, but the configuration of the light source is not limited to this. The light source is not particularly limited provided that it is a light source that can emit the pump beam with frequency $\omega_p$ and the Stokes beam with frequency $\omega_s$ that are needed for the stimulated Raman scattering process. Example modifications of the light source are exemplified below.

Figure 10:
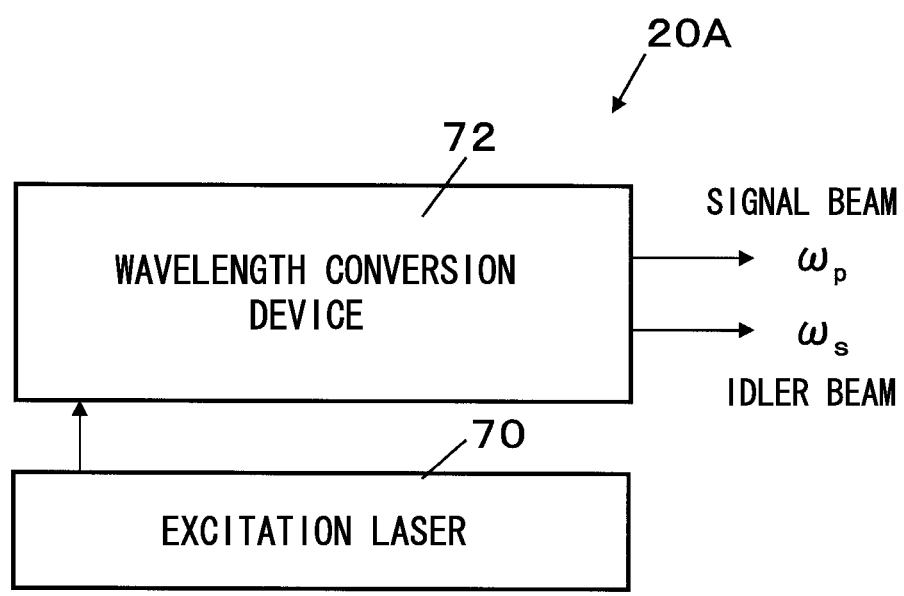
FIG. 10 is a schematic diagram showing a first example modification of a light source.

FIG. 10 is a schematic diagram showing a first example modification of the light source. As shown in FIG. 10, a light source 20A pertaining to the first example modification is equipped with an excitation laser 70 and a wavelength conversion device 72 that converts the wavelength of the beam made incident from the excitation laser 70 and emits beams of two colors.

As the wavelength conversion device 72, for example, an optical parametric oscillator (OPO) that generates laser beams that have been wavelength converted using a nonlinear optical effect is used. In a case where an OPO is used as the wavelength conversion device 72, the wavelength conversion device 72 generates and emits beams of two colors with different frequencies from the beam of one color made incident from the excitation laser 70. The beams of two colors are called a signal beam and an idler beam. Generally the wavelength of the idler beam is longer than the wavelength of the signal beam.

In this case, the signal beam is used as the pump beam with frequency $\omega_p$ and the idler beam is used as the Stokes beam with frequency $\omega_s$. According to this configuration, oscillation is performed by one laser, so the beam with frequency $\omega_p$ and the beam with frequency $\omega_s$ are synchronous and the synchronizing circuit becomes unnecessary. Examples of cases using an OPO as the wavelength conversion device are described below.

Figure 11A:
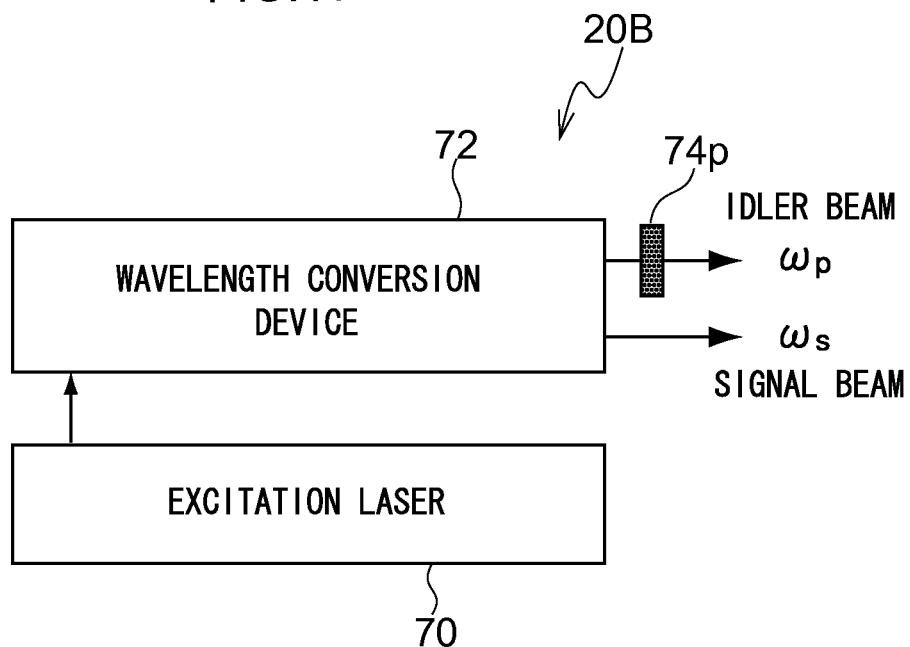
FIG. 11A is a schematic diagram showing a second example modification of the light source.
Figure 11B:
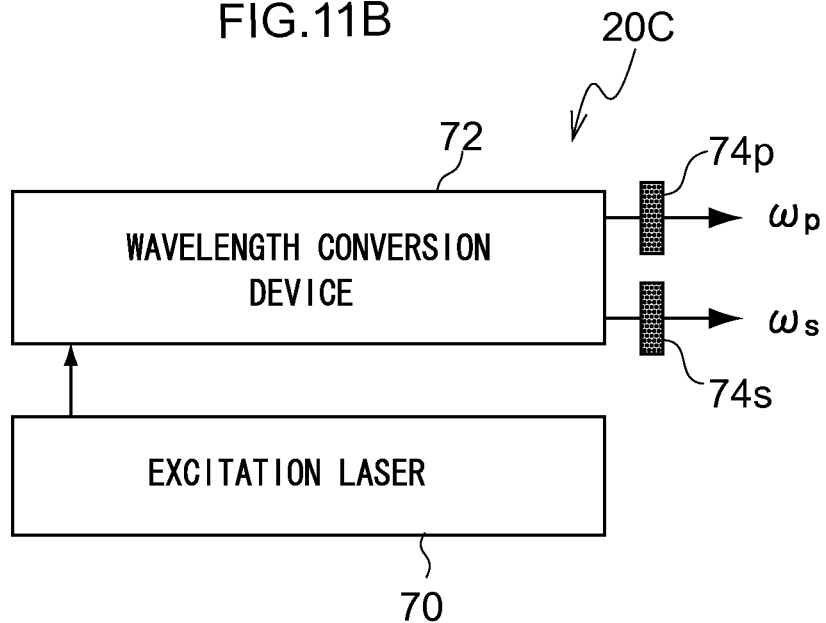
FIG. 11B is a schematic diagram showing an example modification of the light source shown in FIG. 11A.

FIG. 11A is a schematic diagram showing a second example modification of the light source. FIG. 11B is a schematic diagram showing an example modification of the light source shown in FIG. 11A. As shown in FIG. 11A, a light source 20B pertaining to the second example modification is equipped with the excitation laser 70, the wavelength conversion device 72 that converts the wavelength of the beam made incident from the excitation laser 70 and emits beams of two colors (a signal beam and an idler beam), and a wavelength conversion element 74p that is inserted into the optical path of one of the beams of two colors. In this example, the wavelength conversion element 74p is inserted into the optical path of the idler beam. The light source 20B has the same configuration as that of the light source 20A pertaining to the first example modification except that it uses the wavelength conversion element 74p.

As the wavelength conversion element 74p, for example, a nonlinear optical crystal used for second harmonic and third harmonic generation is used. The wavelength of the idler beam transmitted through the wavelength conversion element 74p is converted by the wavelength conversion element 74p to a wavelength that is a whole number fraction—such as ½, ⅓, etc.—of the wavelength when the idler beam exited the wavelength conversion device 72. Here, in a case where the wavelength of the idler beam that has been wavelength converted by the wavelength conversion element 74p is shorter than the wavelength of the signal beam, the idler beam transmitted through the wavelength conversion element 74p is used as the pump beam with frequency $\omega_p$ and the signal beam is used as the Stokes beam with frequency $\omega_s$. According to this configuration, oscillation is performed by one laser, so the beam with frequency $\omega_p$ and the beam with frequency $\omega_s$ are synchronous and the synchronizing circuit becomes unnecessary. Furthermore, measurement becomes possible up to a lower frequency. As shown in FIG. 11B, wavelength conversion elements 74s and 74p may also be inserted into the optical paths of the signal beam and the idler beam.

FIG. 12 is a schematic diagram showing a third example modification of the light source. As shown in FIG. 12, a light source 20D pertaining to the third example modification is equipped with the excitation laser 70, a selectively reflecting mirror 71A, a first wavelength conversion device 72A, a reflecting mirror 71B, a second wavelength conversion device 72B, and selecting means 76. The laser beam emitted from the excitation laser 70 is made incident on the selectively reflecting mirror 71A. The selectively reflecting mirror 71A reflects some of the incident laser beam and transmits the rest.

The laser beam transmitted through the selectively reflecting mirror 71A is reflected by the reflecting mirror 71B and is made incident on the first wavelength conversion device 72A. Beams (a signal beam and an idler beam) of two colors that have been wavelength converted are emitted from the first wavelength conversion device 72A. The laser beam reflected by the selectively reflecting mirror 71A is made incident on the second wavelength conversion device 72B. Beams (a signal beam and an idler beam) of two colors that have been wavelength converted are emitted from the second wavelength conversion device 72B.

The selecting means 76 selects, from among the beams of a maximum of four colors emitted from the first wavelength conversion device 72A and the second wavelength conversion device 72B, beams of two colors to be used as the pump beam and the Stokes beam. As the selecting means 76, for example, an optical filter that selectively transmits beams of two colors is used. In this case, of the two beams selected by the selecting means 76, the beam with the shorter wavelength is used as the pump beam with frequency $\omega_p$ and the other beam is used as the Stokes beam with frequency $\omega_s$. According to this configuration, oscillation is performed by one laser, so the beam with frequency $\omega_p$ and the beam with frequency $\omega_s$ are synchronous and the synchronizing circuit becomes unnecessary. Furthermore, compared to the case of using one wavelength conversion device, the settable range of the frequency difference ($\omega_p - \omega_s$) becomes generally broader because two independent wavelength conversion devices are used.

Figure 22:
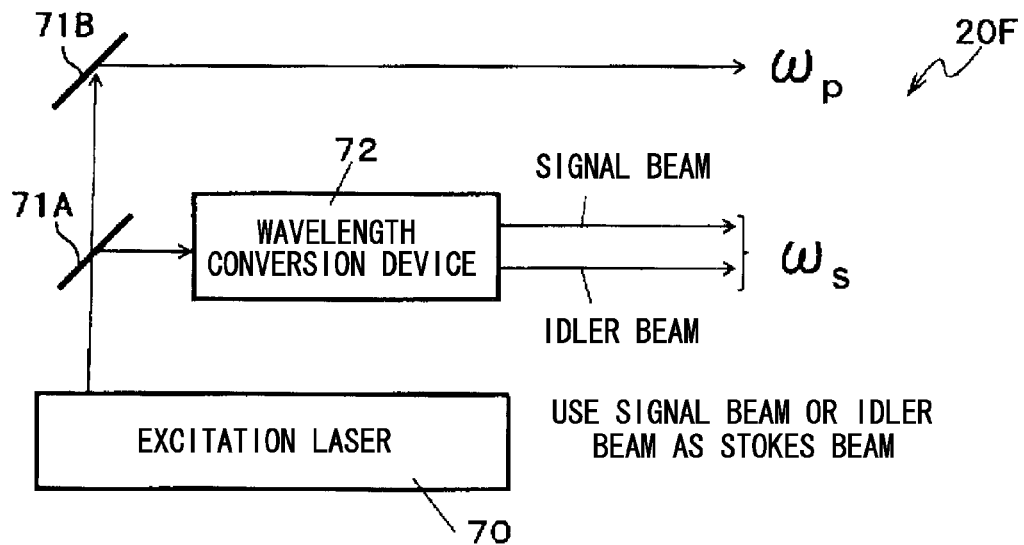
FIG. 22 is a schematic diagram showing a fourth example modification of the light source.

FIG. 22 is a schematic diagram showing a fourth example modification of the light source. As shown in FIG. 22, a light source 20F pertaining to the fourth example modification is equipped with the excitation laser 70, the selectively reflecting mirror 71A, the wavelength conversion device 72, and the reflecting mirror 71B.

The laser beam emitted from the excitation laser 70 is made incident on the selectively reflecting mirror 71A. The selectively reflecting mirror 71A reflects some of the incident laser beam and transmits the rest. The laser beam reflected by the selectively reflecting mirror 71A is made incident on the wavelength conversion device 72. Beams (a signal beam and an idler beam) of two colors that have been wavelength converted are emitted from the wavelength conversion device 72. The laser beam that has been transmitted through the selectively reflecting mirror 71A is reflected in the same direction as the signal beam and the idler beam by the reflecting mirror 71B.

In this case, the beam reflected by the reflecting mirror 71B is used as the pump beam with frequency $\omega_p$ and the signal beam or the idler beam is used as the Stokes beam with frequency $\omega_s$. According to this configuration, oscillation is performed by one laser, so the beam with frequency $\omega_p$ and the beam with frequency $\omega_s$ are synchronous and the synchronizing circuit becomes unnecessary. Furthermore, a pump beam not affected by intensity and phase changes originating in the wavelength conversion device can be obtained.

Furthermore, a wavelength conversion element 74 that converts the wavelength of an incident beam may also be inserted into the optical path of one of the beams of two colors emitted from the wavelength conversion device 72. In the example shown in FIG. 23, a light source 200 has a wavelength conversion element 74. The wavelength conversion element 74 is inserted into the optical path of the signal beam. Except for this, the light source 200 has the same configuration as that of the light source 20F shown in FIG. 22, so the same reference signs are assigned to the same constituent parts and description will be omitted. In this case, beams of three colors including the beam reflected by the reflecting mirror 71B, the wavelength converted signal beam, and the idler beam are obtained.

Figure 24:
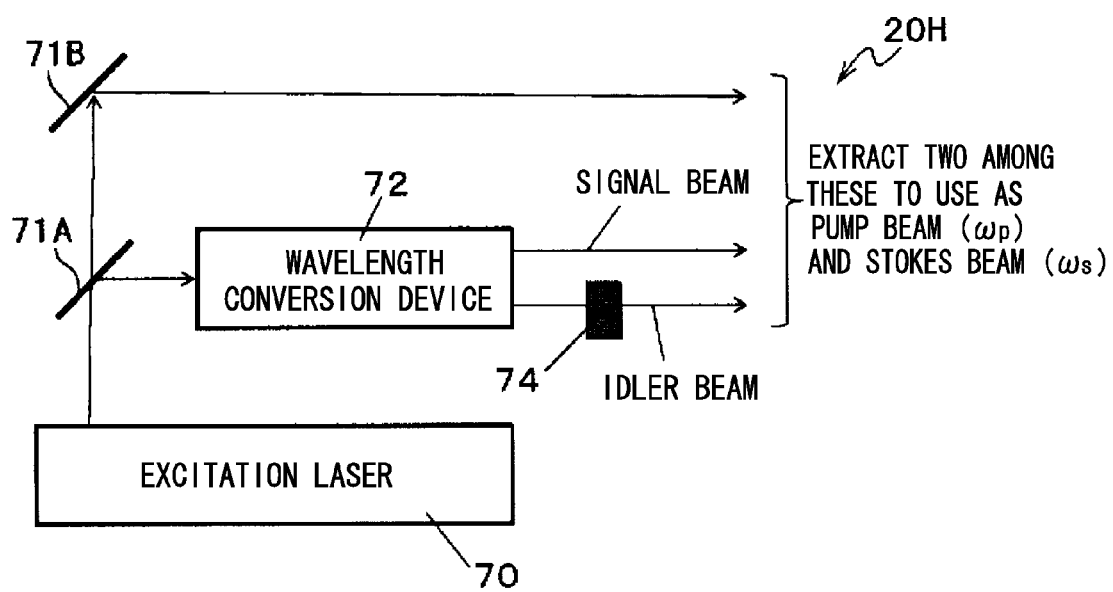
FIG. 24 is a schematic diagram showing another example modification of the light source shown in FIG. 22.

In the example shown in FIG. 24, a light source 20H has a wavelength conversion element 74. The wavelength conversion element 74 is inserted into the optical path of the idler beam. Except for this, the light source 20H has the same configuration as that of the light source 20F shown in FIG. 22, so the same reference signs are assigned to the same constituent parts and description will be omitted. In this case, beams of three colors including the beam reflected by the reflecting mirror 71B, the signal beam, and the wavelength converted idler beam are obtained.

Figure 23:
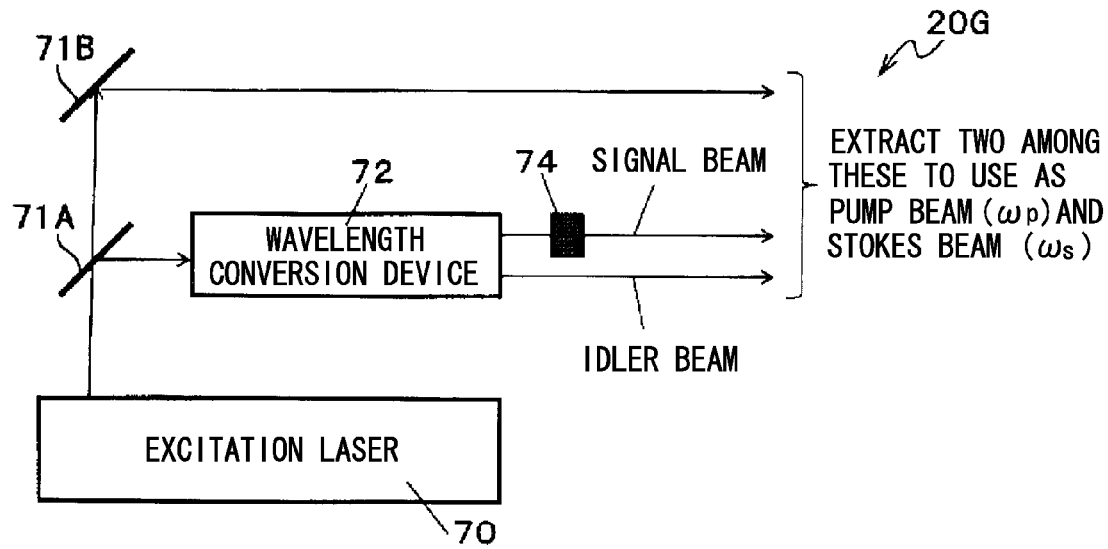
FIG. 23 is a schematic diagram showing an example modification of the light source shown in FIG. 22.

In the examples shown in FIG. 23 and FIG. 24, beams of two colors to be used as the pump beam and the Stokes beam are selected from among beams of three colors by selecting means not shown in the drawings. Of the two selected beams, the beam with the shorter wavelength is used as the pump beam with frequency $\omega_p$ and the other beam is used as the Stokes beam with frequency $\omega_s$. In the examples shown in FIG. 23 and FIG. 24 also, the beam with frequency $\omega_p$ and the beam with frequency $\omega_s$ are synchronous and the synchronizing circuit becomes unnecessary. Furthermore, a pump beam not affected by intensity and phase changes originating in the wavelength conversion device can be obtained.

Figure 13:
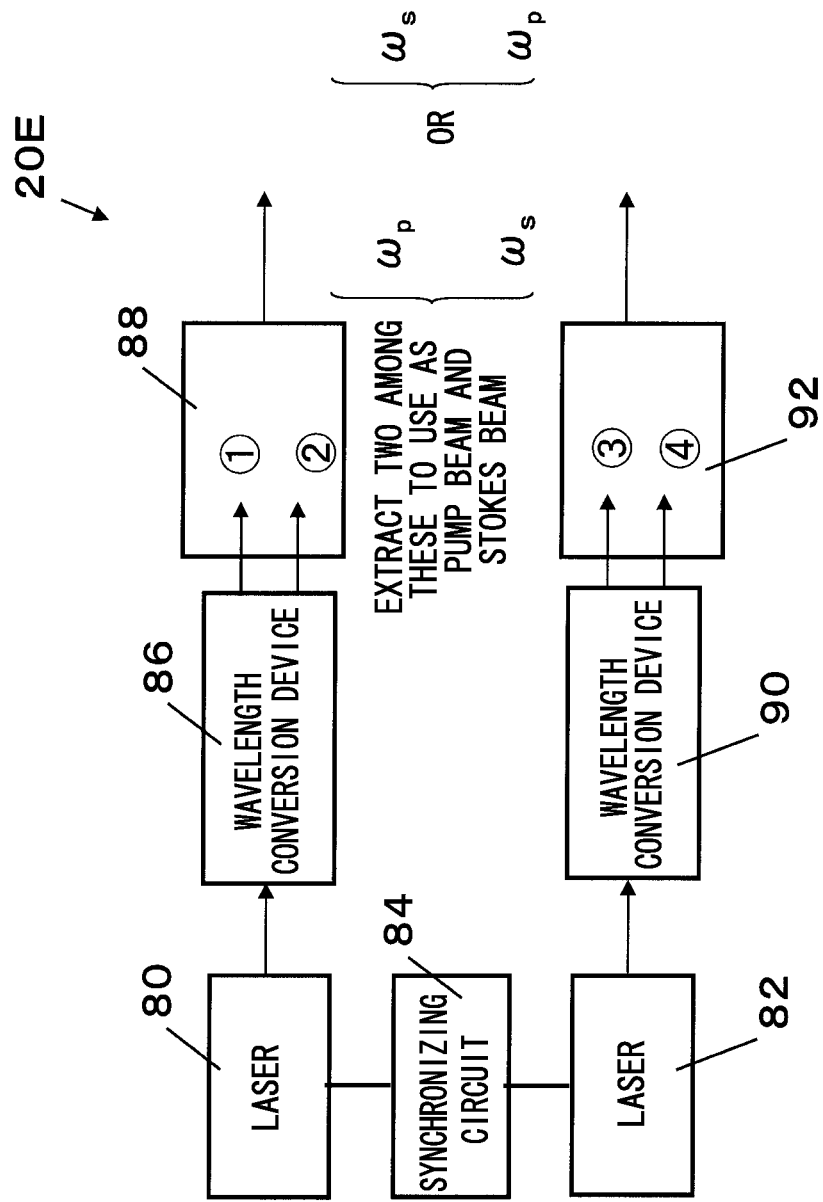
FIG. 13 is a schematic diagram showing a fifth example modification of the light source.

FIG. 13 is a schematic diagram showing of a fifth example modification of the light source. As shown in FIG. 13, a light source 20E pertaining to the fifth example modification is equipped with a first laser 80, a second laser 82, a synchronizing circuit 84 that synchronizes the oscillations of the first laser 80 and the second laser 82, a first wavelength conversion device 86 that converts the wavelength of the beam made incident from the first laser 80 and emits beams (a signal beam and an idler beam) of two colors, a second wavelength conversion device 90 that converts the wavelength of the beam made incident from the second laser 82 and emits beams (a signal beam and an idler beam) of two colors, selecting means 88 that selects a beam of one color from among the beams of two colors emitted from the first wavelength conversion device 86, and selecting means 92 that selects a beam of one color from among the beams of two colors emitted from the second wavelength conversion device 90.

In this case, of the beam selected by the selecting means 88 and the beam selected by the selecting means 92, the beam with the shorter wavelength is used as the pump beam with frequency $\omega_p$ and the other is used as the Stokes beam with frequency $\omega_s$. According to this configuration, the settable range of the frequency difference ($\omega_p - \omega_s$) becomes generally broad and it becomes easy to control the time relationship between the two beams.

In the third example modification (see FIG. 12) and the fifth example modification (see FIG. 13), beams of two colors with frequency $\omega_p$ and frequency $\omega_s$ are obtained using two wavelength conversion devices. In order to simultaneously obtain beams of two colors with frequency $\omega_p$ and frequency $\omega_s$ using one wavelength conversion device, it is necessary to control the crystal temperature in the wavelength conversion device to a constant temperature with which the frequency difference ($\omega_p - \omega_s$) is obtained. If the crystal temperature fluctuates, fluctuations occur in the oscillation wavelength. If the frequency difference ($\omega_p - \omega_s$) cannot be fixed, the stimulated Raman scattering process resulting from resonance cannot be sustained.

In contrast, in a case where two wavelength conversion devices are used, it becomes easy to fix the oscillation wavelength per wavelength conversion device. Furthermore, by using two wavelength conversion devices, the wavelength of one can be set regardless of the wavelength of the other, and it becomes easy to set the wavelengths of both the pump beam and the Stokes beam to 1000 nm or greater.

As the optical parametric oscillator (OPO), an OPO using a form of optical crystal called periodically-poled (abbreviated as "PP crystal") may also be used. With an OPO using a PP crystal, optical path fluctuations that occur when the beam has been wavelength converted are reduced.

Third Embodiment

Next, an optical interferometer pertaining to a third embodiment will be described.

Figure 14:
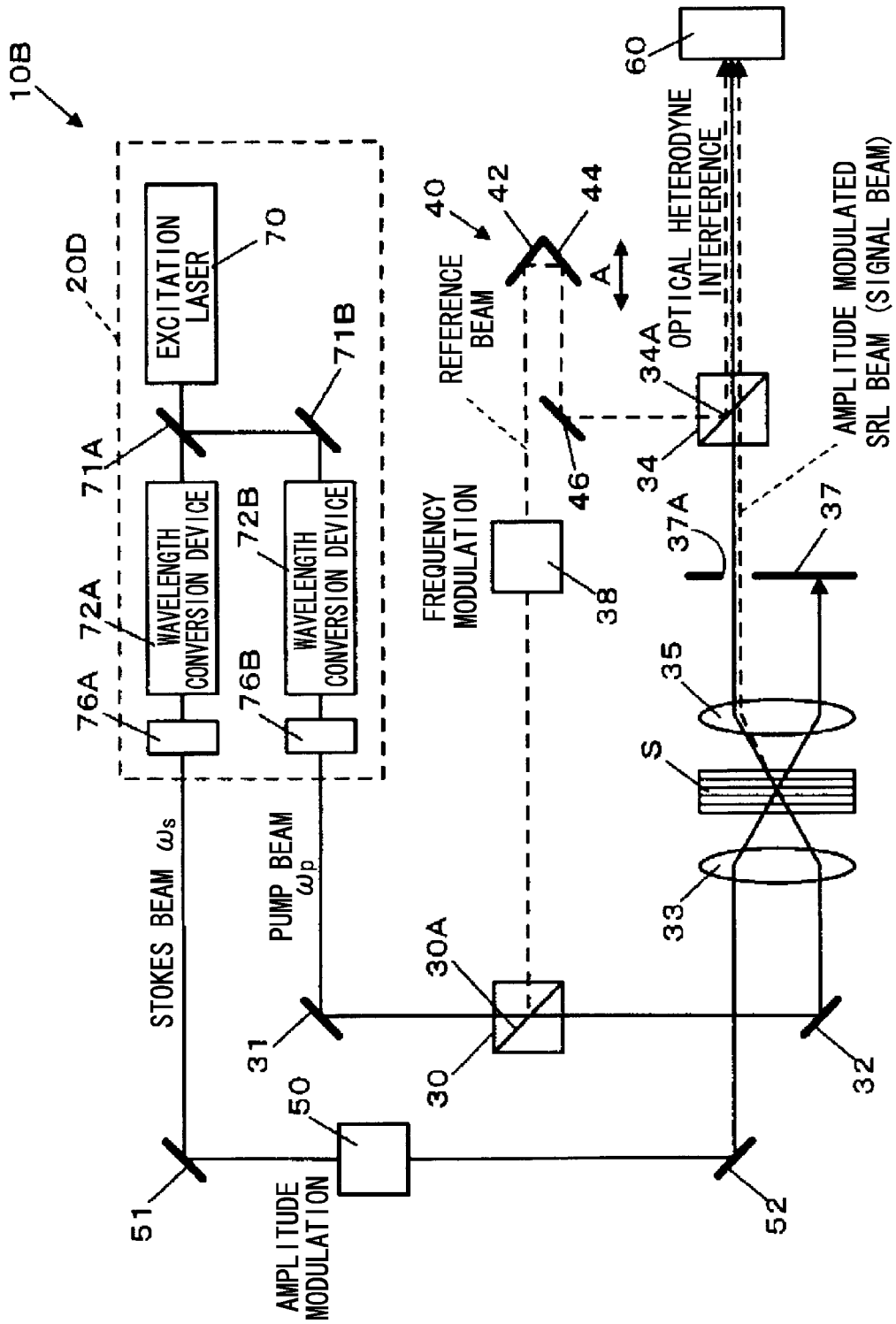
FIG. 14 is a schematic diagram showing an example of the configuration of an optical interferometer pertaining to a third embodiment of the present invention.

FIG. 14 is a schematic diagram showing an example of the configuration of the optical interferometer pertaining to the third embodiment of the present invention. An optical interferometer 10B pertaining to the third embodiment has its various elements disposed in such a way as to configure an off-axis optical system. The configurations and the basic actions of the various elements of the optical interferometer 10B are the same as those of the first embodiment which uses a coaxial optical system, so the same reference signs are assigned to the same constituent parts and description will be omitted.

As shown in FIG. 14, the optical interferometer 10B is equipped with the light source 20D shown in FIG. 12 as the third example modification. The light source 20D is equipped with the excitation laser 70, the selectively reflecting mirror 71A, the first wavelength conversion device 72A, first selecting means 76A, the reflecting mirror 71B, the second wavelength conversion device 72B, and second selecting means 76B. As described below, the light source 20B emits two types of laser beams with different frequencies because of these configurations.

The laser beam emitted from the excitation laser 70 is made incident on the selectively reflecting mirror 71A. The selectively reflecting mirror 71A reflects some of the incident laser beam and transmits the rest. The laser beam transmitted through the selectively reflecting mirror 71A is made incident on the first wavelength conversion device 72A, is wavelength converted, and emits beams of two colors. Of the beams of two colors, the first selecting means 76A transmits the laser beam with frequency $\omega_s$ to be used as the Stokes beam.

The laser beam reflected by the selectively reflecting mirror 71A is reflected by the reflecting mirror 71B, is made incident on the second wavelength conversion device 72B, is wavelength converted, and emits beams of two colors. Of the beams of two colors, the second selecting means 76B transmits the laser beam with frequency $\omega_p$ to be used as the pump beam. In the present embodiment, like in the first embodiment, the laser beam with frequency $\omega_p$ is split into the pump beam and the reference beam.

A reflecting mirror 31 and a beam splitter 30 that has a reflecting surface 30A are disposed on the side of the light source 20B from which the laser beam with frequency $\omega_p$ exits. The laser beam with frequency $\omega_p$ reflected by the reflecting mirror 31 is made incident on the beam splitter 30. The beam splitter 30 uses the reflecting surface 30A to reflect some of the incident beam and transmit the rest of the incident beam. Here, the beam transmitted through the beam splitter 30 is used as the pump beam and the reflected beam is used as the reference beam.

A reflecting mirror 32, a lens 33, a lens 35, a light blocking member 37 that has an aperture 37A, and a beam splitter 34 that has a reflecting surface 34A are disposed in this order from the beam splitter 30 side on the beam transmitting side of the beam splitter 30, that is, on the optical path of the pump beam. In the present embodiment, the sample S is disposed between the lens 33 and the lens 35. In contrast to the first embodiment, the reflecting mirror 32 is not a selectively reflecting mirror but an ordinary reflecting mirror.

A frequency modulation element 38, an optical delay device 40, a reflecting mirror 46, and the beam splitter 34 that has the reflecting surface 34A are disposed in this order from the beam splitter 30 side on the light reflecting side of the beam splitter 30, that is, on the optical path of the reference beam. The optical delay device 40 has a pair of reflecting mirrors 42 and 44 and a mirror driver (not shown in the drawings) such as a piezo element that moves the pair of reflecting mirrors 42 and 44 in the direction of arrow A.

A reflecting mirror 51, an amplitude modulation element 50, a reflecting mirror 52, the lens 33, the lens 35, and the light blocking member 37 that has the aperture 37A are disposed in this order from the light source 20D side on the side of the light source 20D from which the laser beam with frequency $\omega_s$ exits, that is, on the optical path of the Stokes beam.

The beam splitter 34 reflects some or all of the reference beam made incident from one side (the upper side in FIG. 14) of the reflecting surface 34A and transmits some or all of the signal beam made incident from the other side (the left side in FIG. 14) of the reflecting surface 34A. A photodetector 60 is disposed on the reference beam reflecting side (the signal beam transmitting side) of the beam splitter 34.

Because it is the same as in the first embodiment, illustration of the electrical configuration is omitted, but like in the optical interferometer shown in FIG. 4, the photodetector 60 is electrically connected to a signal processor 64. Furthermore, the signal processor 64 is electrically connected to an analyzer 62. Furthermore, the analyzer 62 is also electrically connected to the amplitude modulation element 50. Moreover, the analyzer 62 is electrically connected to an data processor 66.

Next, the actions of the optical interferometer will be briefly described.

In the optical interferometer 10B, the laser beam with frequency $\omega_p$ and the laser beam with frequency $\omega_s$ are emitted from the light source 20D. The laser beam with frequency $\omega_p$ emitted from the light source 20D is reflected by the reflecting mirror 31 and is made incident on the beam splitter 30. The reflecting surface 30A of the beam splitter 30 reflects some of the laser beam with frequency $\omega_p$ and transmits the rest. Here, the reflecting surface 30A of the beam splitter 30 transmits the pump beam and reflects the reference beam. That is, the laser beam with frequency $\omega_p$ is split into the pump beam and the reference beam by the beam splitter 30.

The pump beam transmitted through the reflecting surface 30A of the beam splitter 30 has its optical path bent by the reflecting mirror 32 and is made incident on the lens 33. The incident pump beam is condensed by the lens 33 and is applied to the sample S. The Stokes beam with frequency $\omega_s$ emitted from the light source 20D has its optical path bent by the reflecting mirror 52 and is made incident on the amplitude modulation element 50. The incident Stokes beam has its amplitude modulated by the amplitude modulation element 50. The amplitude modulated Stokes beam has its optical path bent by the reflecting mirror 51 and is made incident on the lens 33. The incident Stokes beam is condensed by the lens 33 and is applied to the sample S.

In the present embodiment, the various optical elements including the lens 33 configure an off-axis optical system as a result of being disposed in such a way that the optical axis of the pump beam and the optical axis of the Stokes beam intersect one another inside the sample S. Consequently, the pump beam and the amplitude modulated Stokes beam are made incident on the lens 33 non-coaxially and are applied in such a way that the optical axes of the beams intersect one another inside the sample S. When the pump beam and the Stokes beam are applied to the sample S, in a case where the stimulated Raman scattering effect resulting from resonance has occurred, the SRG beam and the SRL beam exit from the region of intersection between the pump beam and the Stokes beam inside the sample S. That is, in the present embodiment, the stimulated Raman scattering process is realized with an off-axis optical system.

In a coaxial optical system, the pump beam and the Stokes beam travel on the same optical path. For this reason, in a case where a shielding object is present on the upstream side of the optical path inside the sample S, the scattered beam from the sample S on the downstream side of the optical path becomes unobservable. In contrast, in an off-axis optical system, the pump beam and the Stokes beam travel on different optical paths, and the optical axes of both beams intersect one another inside the sample S. Consequently, the scattered beam from the sample S on the downstream side can be observed without being affected by a shielding object present on the upstream side. For example, even with a sample whose structure cannot be predicted, such as body tissue having nodes, for example, it becomes possible to observe the entire sample.

Furthermore, in a coaxial optical system, the optical paths of the pump beam and the Stokes beam are superposed inside the sample S, and on the optical path inside the sample S, the stimulated Raman scattering beam (signal beam) is generated in all regions exceeding the threshold value of the beam intensity producing the stimulated Raman scattering effect. In contrast, in an off-axis optical system, the stimulated Raman scattering beam is generated only in a narrow region where the pump beam and the Stokes beam are spatially superposed, and the scattered beam is not generated in other regions. Because of this, the generation of false signals from outside the measurement target place is reduced, and the resolution in the beam propagation direction improves. That is, the stimulated Raman scattering beam is observed at the measurement position (the intended depth).

In a case where there is no resonance, the pump beam and the Stokes beam are transmitted the sample S. In a case where there is resonance, in addition to the transmitted pump beam and Stokes beam, the SRG beam and the SRL beam exit from the region of intersection inside the sample S. In FIG. 14, the pump beam and the Stokes beam that are transmitted through the sample S in a case where there is no resonance are depicted by solid lines, and the SRG beam and the SRL beam exiting from the region of intersection inside the sample S in a case where there is resonance are depicted by a dashed line. Although it is not shown in the drawing, the SRG beam generated by resonance travels on the same optical path as that of the Stokes beam transmitted in a case where there is no resonance. The SRG beam and the SRL beam are amplitude modulated at the same frequency as the Stokes beam. The SRG beam, the SRL beam, and the transmitted beam are changed to parallel beams by the lens 35 and are applied to the light blocking member 37.

The pump beam that has been transmitted through the sample S or the SRL beam passes through the aperture 37A disposed in the light blocking member 37. The beam that has passed through the aperture 37A is made incident on the beam splitter 34, is transmitted through the reflecting surface 34A of the beam splitter 34, and is applied to the photodetector 60. Here, the amplitude modulated SRL beam is applied to the photodetector 60 as the signal beam. The Stokes beam that has been transmitted through the sample S or the SRG beam is blocked by the light blocking member 37.

The reference beam reflected by the reflecting surface 30A of the beam splitter 30 is made incident on the frequency modulation element 38 and has its frequency modulated by the frequency modulation element 38. The reference beam whose frequency has been modulated has its optical path length adjusted by the optical delay device 40, has its optical path bent by the reflecting mirror 46, and is made incident on the beam splitter 34. The reference beam whose frequency has been modulated and whose temporal overlap and phase difference with the signal beam have been adjusted is reflected by the reflecting surface 34A of the beam splitter 34 and is applied to the photodetector 60.

In the present embodiment, the SRL beam (signal beam) whose amplitude has been modulated and the reference beam whose frequency has been modulated and whose phase difference with respect to the signal beam has been adjusted undergo optical heterodyne interference. The interference pattern between the signal beam and the reference beam is detected by the photodetector 60.

Like in the first embodiment shown in FIG. 4, the detection signal of the photodetector 60 is input to the signal processor 64. The signal processor 64 processes the input signal and outputs the processed signal to the analyzer 62. The analyzer 62 selectively detects the signal modulated at a specific frequency from the signal input from the signal processor 64. The analyzer 62 outputs the selectively detected signal as the output signal of the optical interferometer.

The configurations described in each of the above embodiments are examples, and it goes without saying that those configurations may also be changed without departing from the gist of the present invention. For example, polarized beams may also be used as the pump beam and the Stokes beam. In this case, elements for polarization control, such as a polarizing beam splitter and various wave plates, are appropriately used. Furthermore, optical fiber, for example, may also be used for beam propagation, mixing, and separation. In this case, elements for beam propagation, mixing, and separation, such as a fiber coupler, are appropriately used. Furthermore, in a case where there is no hindrance to interference, the light source that emits the reference beam may also be a light source separate from the light source that emits the pump beam and the Stokes beam.

The disclosure of Japanese Patent Application No. 2011-218220 is incorporated in its entirety herein by reference. Furthermore, all publications, patent applications, and technical standards mentioned in this specification are incorporated herein by reference to the same extent as if each individual publication, patent application, or technical standard was specifically and individually indicated to be incorporated by reference.

Working Example

The present invention will be described more specifically below by way of a working example. However, the present invention is not limited to this working example.

<Configuration of Optical Interferometer>

An optical interferometer equipped with the same configuration as that of the optical interferometer having the off-axis optical system shown in FIG. 14 was prepared. Details about the main optical elements are given below. For other optical elements, general-purpose optical elements were used.

(1) Excitation Laser 70:

An excitation laser that excites a mode-locked Ti:Sapphire laser using the second harmonic of a Nd:YVO$_4$ laser was used. As the Nd:YVO$_4$ laser, a laser with the product name Verdi-V18 made by Coherent, Inc. was used. As the Ti:Sapphire laser, a laser with the product name Mira-HP made by Coherent, Inc. was used.

(2) Wavelength Conversion Devices 72A and 72B:

Optical parametric oscillators (OPO) using PP crystals were used. As the OPO-I for the pump beam and the OPO-II for the Stokes beam, oscillators with the product name OPO PP Automatic made by Angewandte Physik & Electronik GmbH were used.

(3) Amplitude Modulation Element 50 and Frequency Modulation Element 38:

Electro-optic modulators (EOM) were used. As the EOM for the amplitude modulation element and the EOM for the frequency modulation element, EOMs with the product name M-360-160 (MD) LNB made by Conoptics, Inc. were used.

(4) Optical Delay Device 40:

A fine-motion optical delay device that uses a piezo element to drive retroreflectors fulfilling the equivalent function of a pair of mirrors and rough-motion optical delay devices that mechanically drive retroreflectors fulfilling the equivalent function of a pair of mirrors were combined and used. The fine-motion optical delay device corresponds to the optical delay device 40 in FIG. 14. The rough-motion optical delay devices are disposed in order to adjust optical path lengths. In this working example, the rough-motion optical delay devices were disposed between the frequency modulation element 38 and the optical delay device 40 and between the beam splitter 30 and the reflecting mirror 32. As the fine-motion optical delay device, a device with the product name P-753.11C made by Physik Instrumente GmbH & Co. was used. As the rough-motion optical delay devices, devices with the product name FS-1020X made by Sigma Tech Co., Ltd. were used.

(5) Photodetector 60:

An InGaAs photodiode (PD) was used. The PD was a PD with the product name ET-3040 made by Electro-Optics Technology. Inc.

<Generation of Pump Beam and Stokes Beam>

The mode-locked Ti:Sapphire laser (having a wavelength of 800 nm, a pulse duration of 2 ps, an output of 3.8 W, and a pulse repetition frequency of 76.1 MHz) was excited using the second harmonic (having a wavelength of 532 nm and an output of 14.5 W) of the Nd:YVO$_4$ laser, the obtained output was split into two beams, and the beams were introduced to the OPO-I for the pump beam and the OPO-II for the Stokes beam.

The output of the OPO-I was fixed at a wavelength of 1100 nm and used as the reference beam for obtaining the interference signal and the pump beam in the stimulated Raman scattering process. Below, the reference beam will be called the local oscillator beam (LO) of the OPO-I. The output of the OPO-II was varied in the wavelength range of 1100 nm to 1600 nm. The output wavelength of the OPO-II was changed independent of the output wavelength of the OPO-I. The wavelength of the output beam of the OPO-II was set in such a way that, when $\omega_p$ denoted the frequency of the output beam of the OPO-I and $\omega_s$ denoted the frequency of the output beam of the OPO-II, the natural frequency $\Omega$ of the target molecule in the sample satisfied the relationship of $\Omega=\omega_p-\omega_s$, and the output beam with the set wavelength was used as the Stokes beam.

<Amplitude Modulation of Stokes Beam>

Figure 15:
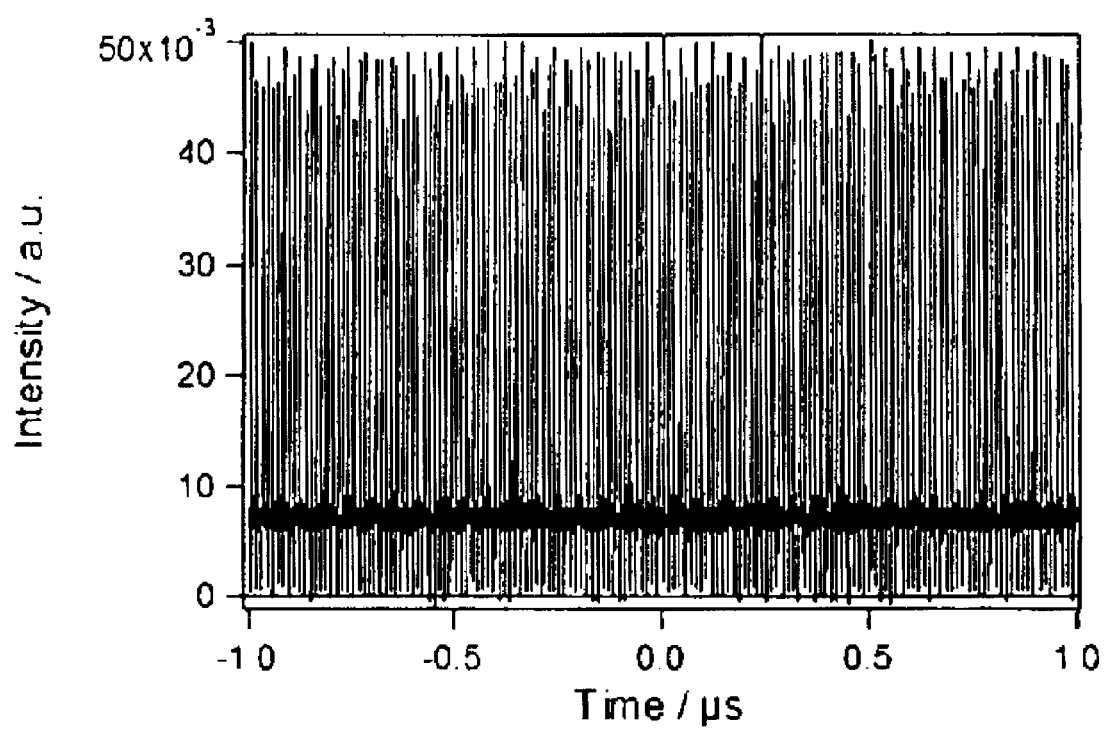
FIG. 15 is a graph showing changes in optical intensity in the time domain of a Stokes beam before amplitude modulation.
Figure 16:
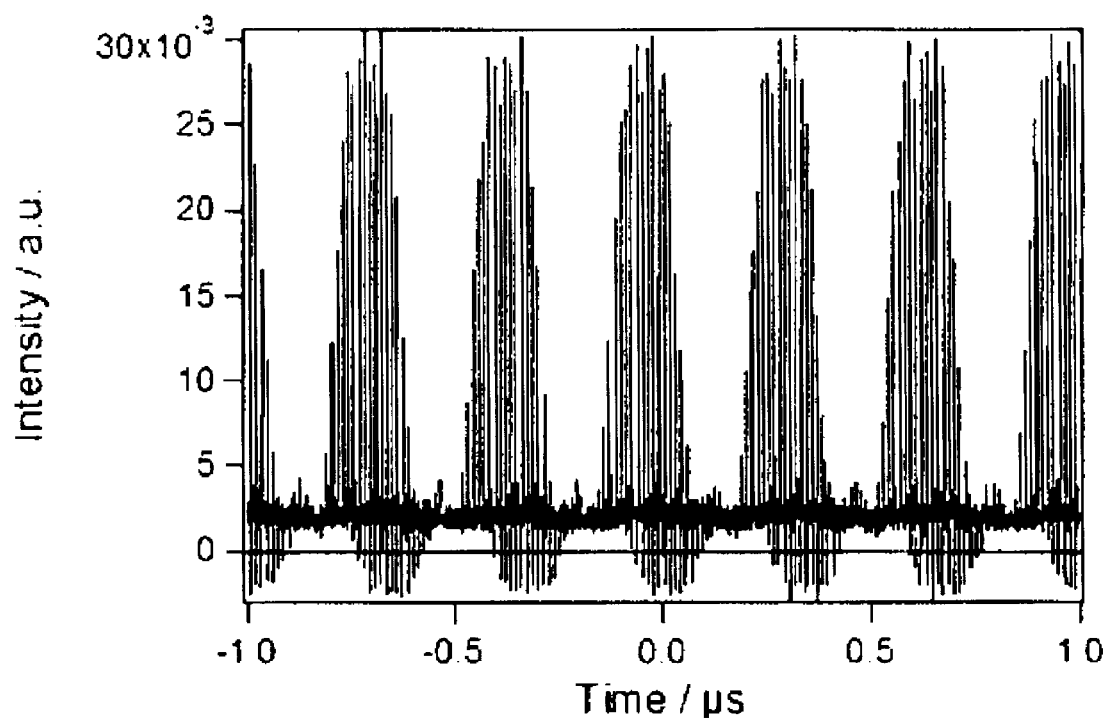
FIG. 16 is a graph showing changes in optical intensity in the time domain of the Stokes beam after amplitude modulation.

FIG. 15 shows the result of detecting the output (Stokes beam) from the OPO-II with the InGaAs photodiode and introducing it to an oscilloscope (product name MDO 4104-6 made by Tektroniks). The vertical axis represents beam intensity. The unit is an arbitrary unit (a.u.). The horizontal axis represents time. The unit is microseconds (µs). It will be understood that, as shown in FIG. 15, the beam pulse is output from the OPO-II at intervals of 13 nanoseconds (ns) and the intensity is substantially uniform. FIG. 16 shows the result of modulating this output by a sine function of 3 MHz using the EOM for amplitude modulation. Like in FIG. 15, the vertical axis represents beam intensity and the horizontal axis represents time. It will be understood that, as shown in FIG. 16, the intensity of the beam pulse periodically changes and six cycles are included in the time of 2 microseconds (µs). The frequency of this change corresponds to 3 MHz.

<Frequency Modulation of Reference Beam>

Figure 17:
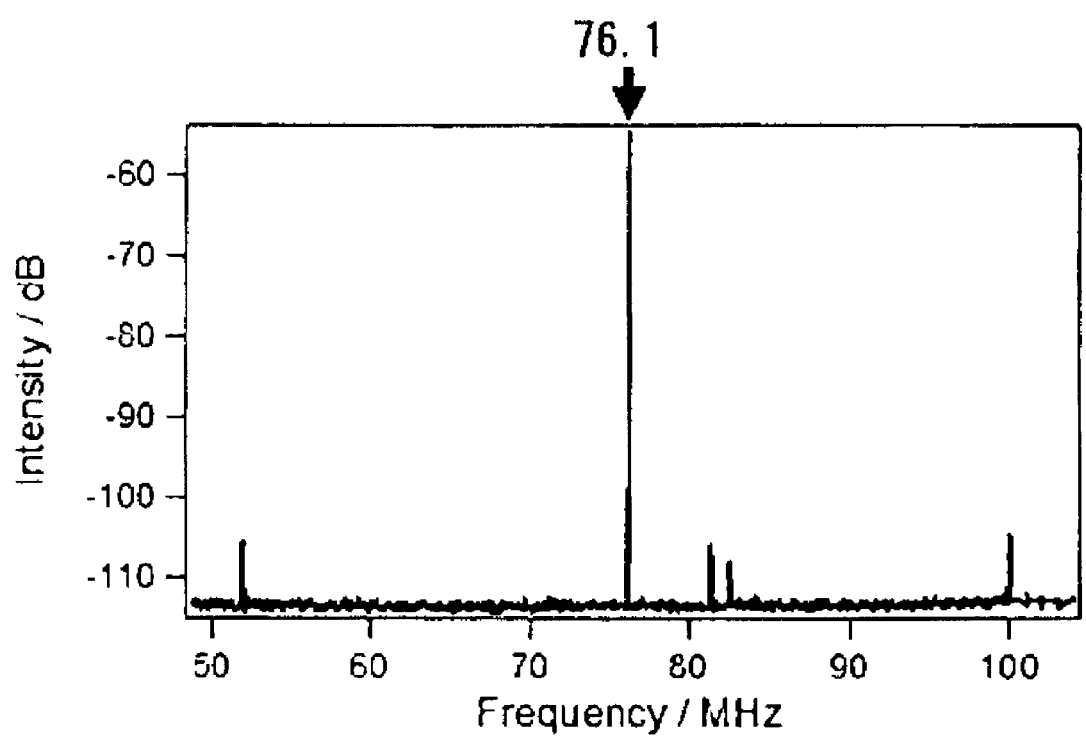
FIG. 17 is a graph showing changes in optical intensity in the frequency domain of a reference beam before frequency modulation.
Figure 18:
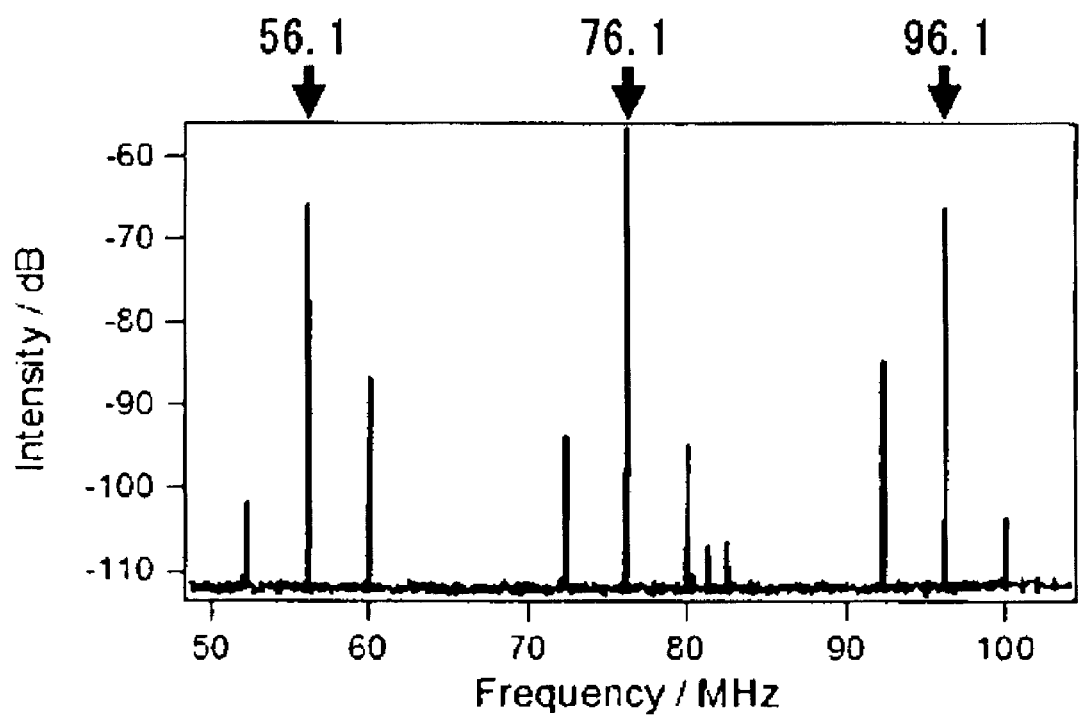
FIG. 18 is a graph showing changes in optical intensity in the frequency domain of the reference beam after frequency modulation.

FIG. 17 shows the result of introducing the local oscillator beam (LO) of the OPO-I unmodulated by the EOM for frequency modulation to the mixed domain oscilloscope (product name MDO 4104-6 made by Tektroniks) to obtain a spectrum in the frequency domain. The vertical axis represents beam intensity. The unit is decibels (dB). The horizontal axis represents frequency. The unit is MHz. In the spectrum shown in FIG. 17, the sharp band seen at 76.1 MHz corresponds to the pulse repetition frequency of the laser. FIG. 18 shows the result of modulating this output by a sine function of 20 MHz using the EOM for frequency modulation. Like in FIG. 17, the vertical axis represents beam intensity and the horizontal axis represents frequency. It will be understood that, as shown in FIG. 18, bands are seen at frequencies of 56.1 MHz and 96.1 MHz and the laser output of the original frequency 76.1 MHz is being modulated by 20 MHz. That is, it was positively demonstrated that it is possible to modulate the frequency by several tens of MHz using the EOM.

<Detection of Stimulated Raman Scattering Signal>

Figure 19:
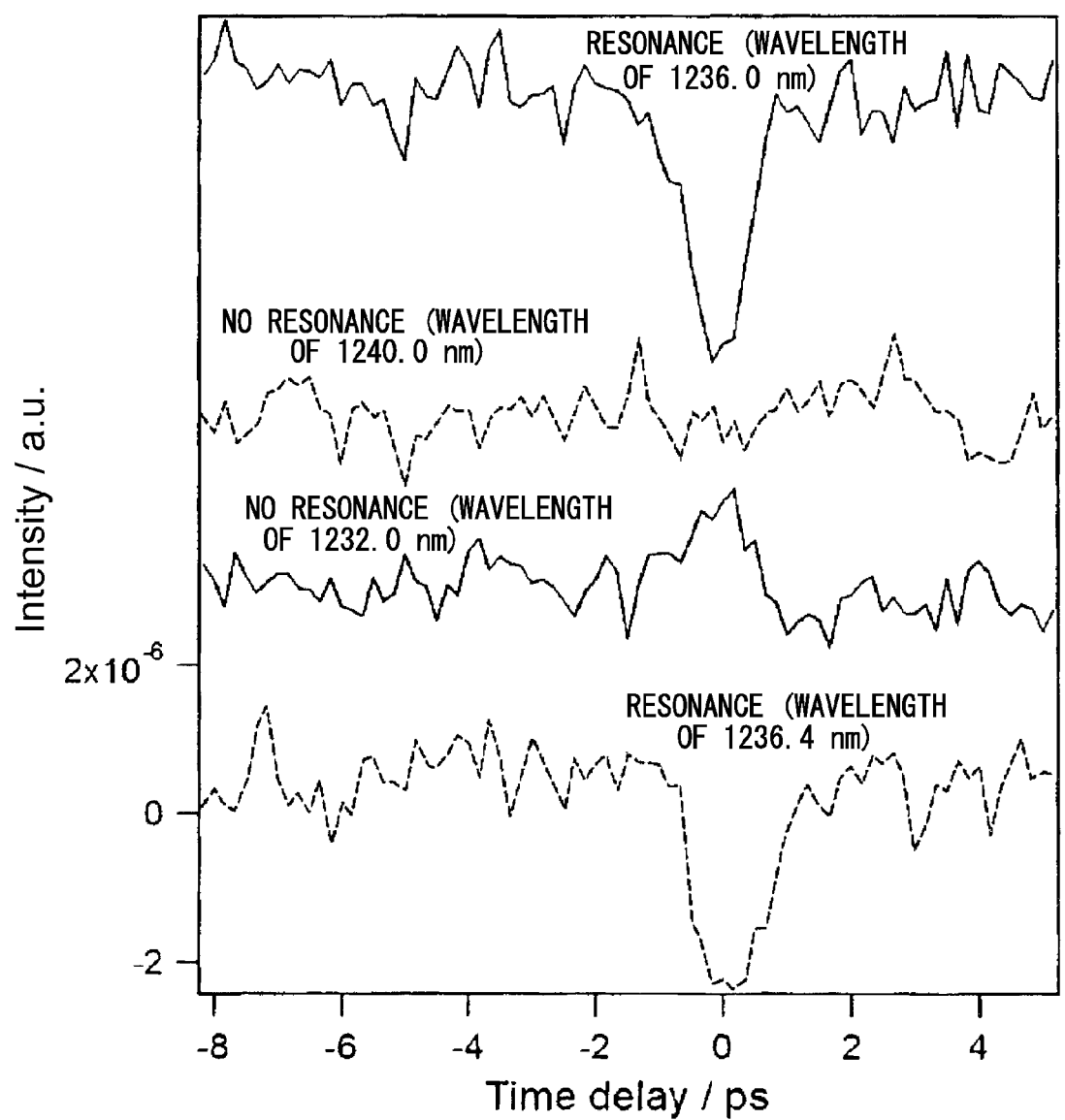
FIG. 19 is a graph showing detection results of a stimulated Raman scattering signal.

Using polystyrene film (product name OPS Film (GM Grade) made by Asahi Kasei Chemical Corporation; having a thickness of 100 µm (=25 µm×four layers)) as the test sample, the natural frequency (1003 cm$^{-1}$) of the breathing vibration of the phenyl rings in the polystyrene was selected as the resonance target of stimulated Raman scattering. The pump beam and the Stokes beam were applied while the wavelength of the pump beam was fixed at 1100 nm and the wavelength of the Stokes beam was varied in the range of 1100 nm to 1600 nm. The pump beam and the Stokes beam were applied in such a way that both beams intersected one another inside the sample. FIG. 19 shows the result of sweeping the time delay of the pump beam and the Stokes beam. The vertical axis represents beam intensity. The unit is an arbitrary unit (a.u.). The horizontal axis represents time delay. The unit is picoseconds (ps).

As shown in FIG. 19, there was resonance when the wavelength of the Stokes beam was 1236.0 nm (a frequency difference of 1000.3 cm$^{-1}$), and a signal resulting from downward stimulated Raman scattering (a stimulated Raman loss) was obtained in the vicinity of the time delay of 0 ps. Furthermore, there was no resonance when the wavelength of the Stokes beam became 1240.0 nm (a frequency difference of 1026.4 cm$^{-1}$) and 1232.0 nm (a frequency difference of 974.0 cm$^{-1}$), and the signal resulting from stimulated Raman scattering disappeared. When the wavelength of the Stokes beam was returned to 1236.4 nm (a frequency difference of 1002.9 cm$^{-1}$), the resonance reappeared and a signal resulting from stimulated Raman scattering was obtained. That is, the stimulated Raman scattering signal could be observed from inside the sample using near-infrared beams of 1000 nm or higher for both the pump beam and the Stokes beam.

<Acquisition of Stimulated Raman Scattering Interference Signal>

As described above, an observation of the interference signal resulting from the optical heterodyne interference between the stimulated Raman scattering beam and the reference beam was performed using the natural frequency (1003 cm$^{-1}$) of the breathing vibration of the phenyl rings in the polystyrene as the resonance target of stimulated Raman scattering. The output of the OPO-I was fixed at a wavelength of 1100 nm and used as the pump beam and the reference beam (local oscillation beam LO) in the stimulated Raman scattering process. The output of the OPO-II was fixed at a wavelength of 1236 nm and used as the Stokes beam in the stimulated Raman scattering process. The amplitude of the Stokes beam was modulated by a sine function of 3 MHz using the EOM. The frequency of the reference beam LO was modulated by a sine function of 10 MHz using the EOM.

The pump beam and the amplitude modulated Stokes beam were condensed in such a way that their optical axes intersected one another inside the sample and were applied to the test sample, whereby the stimulated Raman scattering process resulting from resonance was realized. The beam with wavelength 1100 nm observed from the test sample came to include a stimulated Raman loss signal (SRL beam) that repeatedly increased and decreased at a frequency of 3 MHz. The SRL beam and the frequency modulated reference beam LO were made incident on the photodetector with their optical axes put together in such a way that the SRL beam and the reference beam LO were superposed on the light receiving surface of the photodetector.

The SRL beam and the frequency modulated reference beam LO underwent optical heterodyne interference, whereby an interference signal with a frequency of f±f' equal to the sum of or difference between the beat frequency f and the amplitude modulated frequency f' of the Stokes beam was detected. Here, an interference signal with frequency $F_{i\text{-}SRS}$ at the time of resonance was detected. The frequency $F_{i\text{-}SRS}$ is given by the following equation.

$$F_{i\text{-}SRS} = 76.1 \pm 10 \pm 3 \text{ (MHz)} \quad \text{[Equation 4]}$$

Here, 76.1 MHz is the repetition frequency of the original laser beam pulse. 10 MHz is the modulation frequency f applied to the reference beam LO. 3 MHz is the modulation frequency f' applied to the Stokes beam.

The detection frequency of the mixed domain oscilloscope was adjusted to the range of 63.1±0.1 MHz. Because of this, the interference signal with frequency $F_{i\text{-}SRS}$ was extracted.

Figure 20:
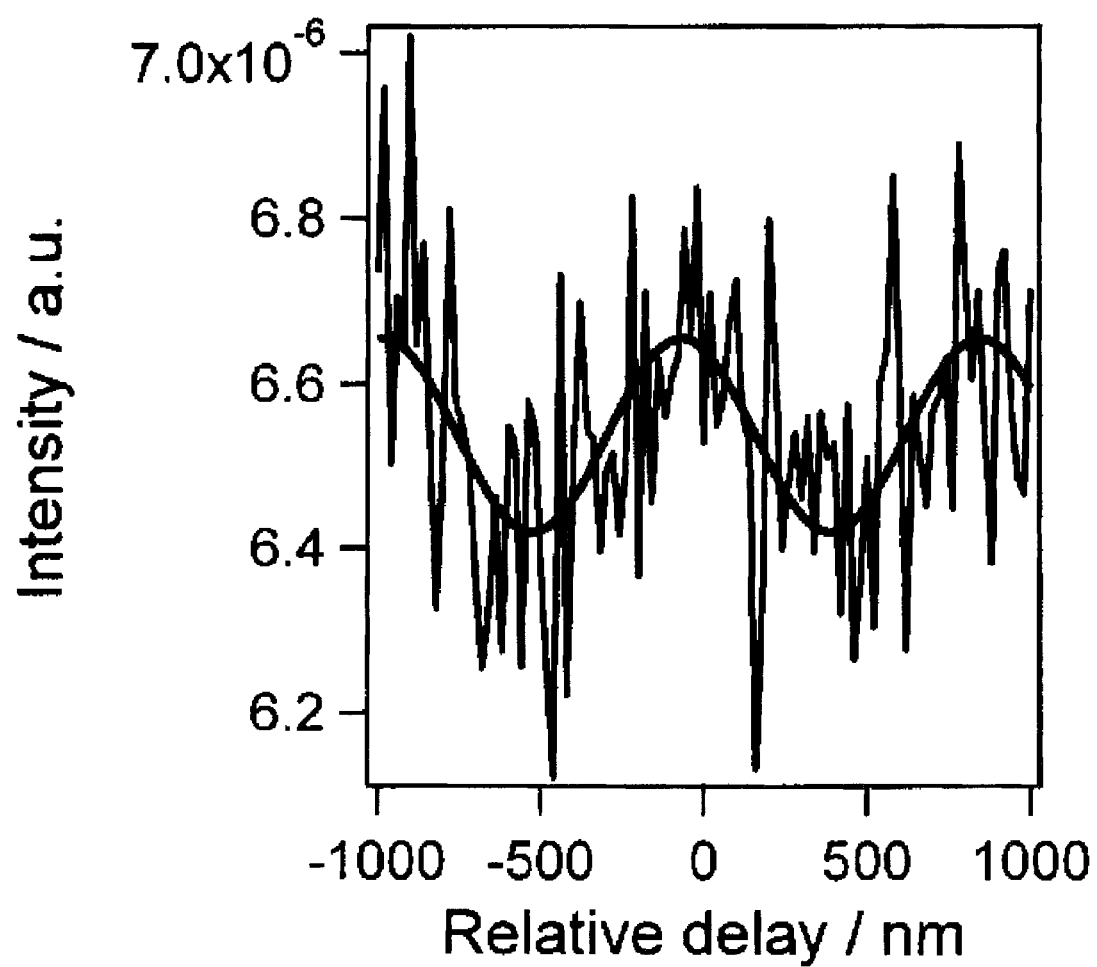
FIG. 20 is a graph showing observation results (when there is resonance) of an interference signal.

FIG. 20 shows the result of plotting the beam intensity of the observed interference signal while using the fine-motion optical delay device to vary the delay between the SRL beam and the reference beam LO 10 nm at a time. The vertical axis represents beam intensity. The unit is an arbitrary unit (a.u.). The horizontal axis represents relative delay. The unit is nm. Furthermore, the wavelength of the pump beam was set to 1100 nm, the wavelength of the Stokes beam was set to 1236 nm, and stimulated Raman scattering resulting from resonance with respect to the natural frequency of 1000.3 cm$^{-1}$ was observed.

Because the interference signal was faint, integration was performed for one hour. Furthermore, the result of fitting the interference signal in a sine function using the least square method was indicated at the same time by a fat solid line. As seen in FIG. 20, although it is faint at the current point in time, an interference pattern between the SRL beam and the reference beam LO was observed.

Figure 21:
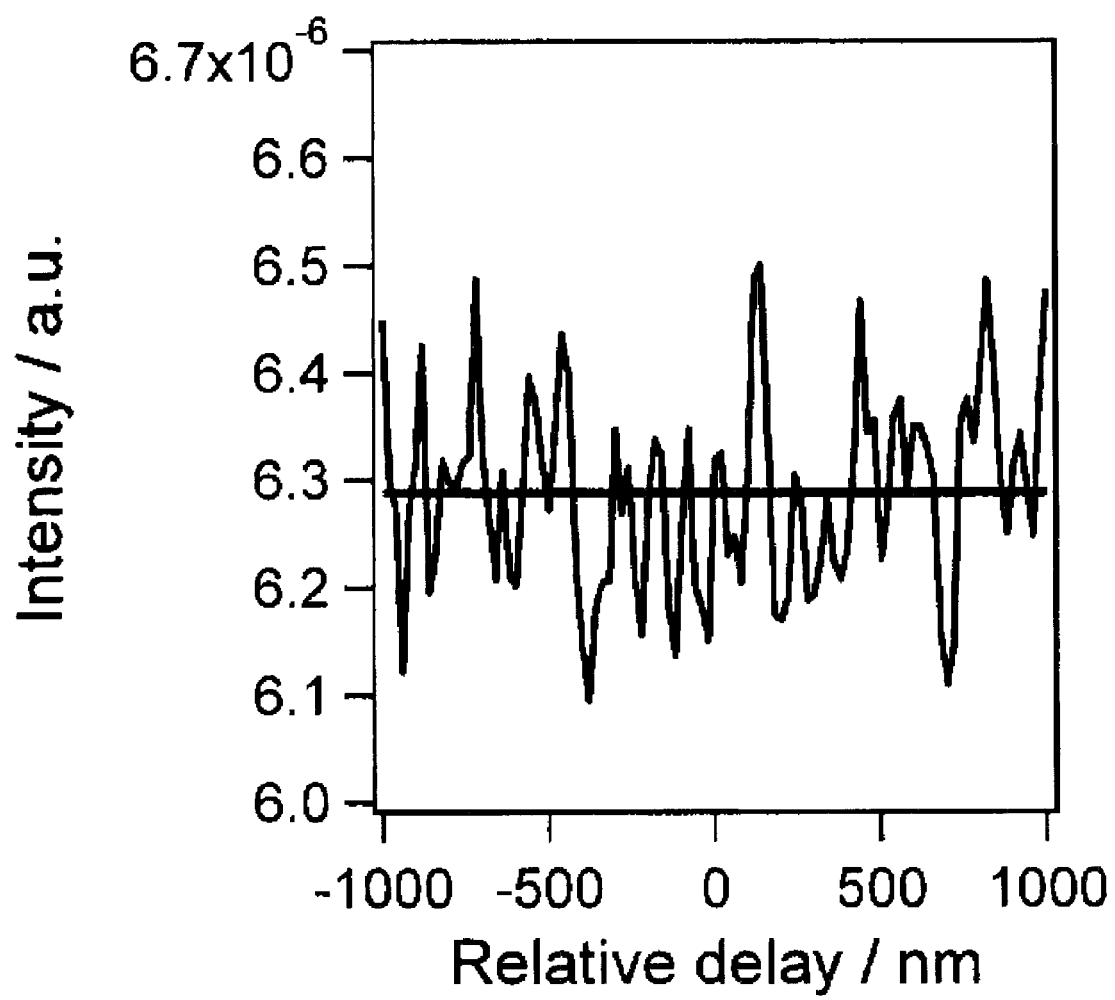
FIG. 21 is a graph showing observation results (when there is no resonance) of the interference signal.

The interference pattern between the SRL beam and the reference beam LO was observed only in a case where stimulated Raman scattering resulting from resonance was occurring. When there was no resonance, the SRL beam was not generated, and as shown in FIG. 21 only noise was observed. Like in FIG. 20, the vertical axis represents beam intensity and the horizontal axis represents relative delay. The wavelength of the pump beam was set to 1100 nm and the wavelength of the Stokes beam was set to 1230 nm. At this time, the frequency difference between the pump beam and the Stokes beam was 960.8 cm$^{-1}$ and there was no resonance.

The invention claimed is:

1. An optical interferometer comprising:
   a light source that emits a coherent pump beam with a first optical frequency and emits a Stokes beam with a second optical frequency that has, with respect to the first optical frequency, a frequency difference corresponding to a natural frequency of a target molecule;
   an amplitude modulating unit that applies a periodic amplitude modulation at a third frequency to the Stokes beam;
   a splitting unit that splits the pump beam into a reference beam and an applied pump beam;
   a frequency modulating unit that applies a frequency modulation at a fourth frequency to the reference beam;
   an optical path length adjusting unit that adjusts the optical path length of the reference beam; and
   a detecting unit into which is inputted (i) an applied Stokes beam, which is the Stokes beam to which the periodic amplitude modulation has been applied, and (ii) a signal beam, which is the applied pump beam following a stimulated Raman loss or a stimulated Raman gain in accordance with the periodic amplitude modulation of the applied Stokes beam as a result of the frequency difference between the applied pump beam and the applied Stokes beam resonating with the target molecule when the applied pump beam and the applied Stokes beam have been applied to a measurement position of an object, and wherein the detecting unit detects a heterodyne interference pattern between the signal beam and the reference beam to which the frequency modulation has been applied.

2. The optical interferometer according to claim 1, wherein the applied pump beam that has experienced the stimulated Raman loss in accordance with the periodic amplitude modulation is used as the signal beam.

3. The optical interferometer according to claim 1, wherein the applied Stokes beam that has experienced the stimulated Raman gain in accordance with the periodic amplitude modulation is used as the signal beam.

4. The optical interferometer according to claim 1, wherein the light source has a first laser that emits the pump beam, a second laser that emits the Stokes beam, and a synchronizing circuit that synchronizes oscillation of the first laser and oscillation of the second laser.

5. The optical interferometer according claim 1, wherein the light source has one laser and a wavelength conversion device that converts the wavelength of the beam emitted from the one laser to thereby generate the pump beam and the Stokes beam.

6. The optical interferometer according to claim 1, wherein the light source has one laser, a wavelength conversion device that converts the wavelength of the beam emitted from the one laser to thereby generate two coherent beams with different wavelengths, and at least one wavelength conversion element that is disposed on a beam exiting side of the wavelength conversion device and converts the wavelength of at least one of the two coherent beams with different wavelengths.

7. The optical interferometer according to claim 1, wherein the light source has one laser, a splitting unit that splits the beam emitted from the one laser into two beams, a first wavelength conversion device that converts the wavelength of one beam that has been split to thereby generate two coherent beams with different wavelengths, a second wavelength conversion device that converts the wavelength of the other beam that has been split to thereby generate two coherent beams with different frequencies, and a selecting unit that selects two coherent beams from among the four coherent beams generated by the first wavelength conversion device and the second wavelength conversion device.

8. The optical interferometer according to claim 1, wherein the light source has a first laser, a second laser, a synchronizing circuit that synchronizes the oscillation of the first laser and the oscillation of the second laser, a first wavelength conversion device that converts the wavelength of the beam emitted from the first laser to thereby generate two coherent beams with different wavelengths, a first selecting unit that selects one coherent beam from among the two coherent beams generated by the first wavelength conversion device, a second wavelength conversion device that converts the wavelength of the beam emitted from the second laser to thereby generate two coherent beams with different wavelengths, and a second selecting unit that selects one coherent beam from among the two coherent beams generated by the second wavelength conversion device.

9. The optical interferometer according to claim 1, wherein the light source has one laser, a splitting unit that splits the beam emitted from the one laser into two beams, a first wavelength conversion device that converts the wavelength of one beam that has been split to thereby generate two coherent beams with different wavelengths, and a selecting unit that selects two coherent beams from among three coherent beams comprising the other beam that has been split and the two coherent beams generated by the first wavelength conversion device.

10. The optical interferometer according to claim 1, further comprising a measuring unit that measures a change in an intensity of the applied Stokes beam that has experienced the stimulated Raman loss or the stimulated Raman gain in accordance with the periodic amplitude modulation.

* * * * *

UNITED STATES PATENT AND TRADEMARK OFFICE
CERTIFICATE OF CORRECTION

| | | |
|---|---|---|
| PATENT NO. | : 9,599,454 B2 | Page 1 of 1 |
| APPLICATION NO. | : 14/348495 | |
| DATED | : March 21, 2017 | |
| INVENTOR(S) | : Hiroharu Yui | |

It is certified that error appears in the above-identified patent and that said Letters Patent is hereby corrected as shown below:

In the Claims

At Column 28, Line 61, "according claim" should be -- according to claim --.

Signed and Sealed this
Nineteenth Day of September, 2017

Joseph Matal
*Performing the Functions and Duties of the
Under Secretary of Commerce for Intellectual Property and
Director of the United States Patent and Trademark Office*